US011389526B2

(12) United States Patent
Zeng et al.

(10) Patent No.: US 11,389,526 B2
(45) Date of Patent: *Jul. 19, 2022

(54) SELF-ATTENUATED PROPHYLACTIC AND THERAPEUTIC VACCINES AGAINST PATHOGENS

(71) Applicant: Texas Tech University System, Lubbock, TX (US)

(72) Inventors: Mingtao Zeng, El Paso, TX (US); Ke Wen, Harrison, NY (US)

(73) Assignee: Texas Tech University System, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/048,714

(22) PCT Filed: Apr. 18, 2019

(86) PCT No.: PCT/US2019/028065

§ 371 (c)(1),
(2) Date: Oct. 19, 2020

(87) PCT Pub. No.: WO2019/204571

PCT Pub. Date: Oct. 24, 2019

(65) Prior Publication Data

US 2021/0236622 A1 Aug. 5, 2021

Related U.S. Application Data

(60) Provisional application No. 62/660,327, filed on Apr. 20, 2018.

(51) Int. Cl.

| | |
|---|---|
| ***A61K 39/145*** | (2006.01) |
| ***A61K 39/39*** | (2006.01) |
| ***C12N 15/113*** | (2010.01) |
| ***C12N 7/00*** | (2006.01) |
| *A61K 39/00* | (2006.01) |

(52) U.S. Cl.

CPC ............ *A61K 39/145* (2013.01); *A61K 39/39* (2013.01); *C12N 7/00* (2013.01); *C12N 15/1131* (2013.01); *A61K 2039/5254* (2013.01); *A61K 2039/53* (2013.01); *C12N 2310/141* (2013.01); *C12N 2760/16134* (2013.01)

(58) Field of Classification Search

CPC .............. C12N 2310/141; C12N 15/86; C12N 15/1137; C12N 15/87; C12N 15/85; C12N 2320/50; C12N 2330/10; C12N 2330/51; C12N 2760/16111; C12N 2799/021; C12N 2760/16134; A61K 2039/5254; A61K 39/145; A61P 31/12

See application file for complete search history.

(56) References Cited

U.S. PATENT DOCUMENTS

| | | | | |
|---|---|---|---|---|
| 8,883,995 B2 | 11/2014 | tenOever | | |
| 10,493,146 B2 * | 12/2019 | Zeng | ...................... | C12N 15/86 |
| 2017/0232097 A1 | 8/2017 | Zeng et al. | | |

FOREIGN PATENT DOCUMENTS

| | | |
|---|---|---|
| WO | 2010/110914 A2 | 9/2010 |
| WO | 2016/061200 A1 | 4/2016 |

OTHER PUBLICATIONS

Seitz et al. Transfue Med. Hemother. May 2016, vol. 43 (3). pp. 203-222.*
Liang Hepatology, 2019, 49(5 Suppl): S13-S21.*
Abraham S et al. Long-term engraftment of human natural T regulatory cells in NOD/SCID IL2rgammac(null) mice by expression of human IL-2. PLoS One. 2012;7(12):e51832.
Arévalo MT et al. Targeted Silencing of Anthrax Toxin Receptors Protects against Anthrax Toxins. The Journal of biological chemistry. 2014;289(22):15730-8.
Boltz DA et al. Oseltamivir prophylactic regimens prevent H5N1 influenza morbidity and mortality in a ferret model. J Infect Dis. 2008;197(9):1315-23.
Bouvier NM et al. Animal Models for Influenza Virus Pathogenesis and Transmission. Viruses. 2010;2(8):1530-63.
Cellerai C et al. Proliferation capacity and cytotoxic activity are mediated by functionally and phenotypically distinct virus-specific CD8 T cells defined by interleukin-7R{alpha} (CD127) and perforin expression. J Virol. 2010;84(8):3868-78.
Corti D et al. Broadly neutralizing antiviral antibodies. Annu Rev Immunol. 2013;31:705-42. doi: 10.1146/annurev-immunol-032712-095916.
D'Cruz OJ et al. Intravaginal toxicity studies of a gel-microemulsion formulation of spermicidal vanadocenes in rabbits. Toxicol Appl Pharmacol. 2001;170(2):104-12.
D'Cruz OJ et al. Mucosal toxicity studies of a gel formulation of native pokeweed antiviral protein. Toxicol Pathol. 2004;32(2):212-21.
Donnelly S et al. Whole-cell but not acellular pertussis vaccines induce convulsive activity in mice: evidence of a role for toxin-induced interleukin-1beta in a new murine model for analysis of neuronal side effects of vaccination. Infect Immun. 2001;69(7):4217-23.
Duan S et al. Oseltamivir-resistant pandemic H1N1/2009 influenza virus possesses lower transmissibility and fitness in ferrets. PLoS pathogens. 2010;6(7):e1001022.

(Continued)

*Primary Examiner* — Bao Q Li

(74) *Attorney, Agent, or Firm* — Edwin S. Flores; Daniel J. Chalker; Chalker Flores, LLP

(57) ABSTRACT

The present invention includes a live, self-attenuated therapeutic vaccine, virus and methods of making and using the same, comprising: an isolated virus comprising a viral genome that expresses one or more viral antigens; and an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells.

25 Claims, 9 Drawing Sheets

Specification includes a Sequence Listing.

(56) References Cited

OTHER PUBLICATIONS

Dugan VG et al. Update: Influenza Activity—United States, Oct. 1-Nov. 25, 2017.
Hao, Linhui, et al., '*Drosophila* RNAi screen identifies host genes important for influenza virus replication', 2008, Nature, vol. 454, pp. 890-893.
Harari A et al. Distinct profiles of cytotoxic granules in memory CD8 T cells correlate with function, differentiation stage, and antigen exposure. J Virol. 2009;83(7):2862-71.
Harmon MW et al. Antibody response in humans to influenza virus type B host-cell-derived variants after vaccination with standard (egg-derived) vaccine or natural infection. J Clin Microbiol. 1988;26(2):333-7.
Hensley SE. Challenges of selecting seasonal influenza vaccine strains for humans with diverse pre-exposure histories. Current opinion in virology. 2014;8C:85-9.
International Search Report [ISA/AU] PCT/US2019/028065 dated Jul. 29, 2019.
Ison MG. Antivirals and resistance: influenza virus. Current opinion in virology. 2011;1(6):563-73.
Jackson LA et al. Immunogenicity of an inactivated monovalent 2009 H1N1 influenza vaccine in pregnant women. J Infect Dis. 2011;204(6):854-63.
Jagger BW et al. An overlapping protein-coding region in influenza A virus segment 3 modulates the host response. Science (New York, NY). 2012;337(6091):199-204.
Karlas A et al. Genome-wide RNAi screen identifies human host factors crucial for influenza virus replication. Nature. 2010;463(7282):818-22.
Keitel WA et al. Safety and immunogenicity of inactivated, Vero cell culture-derived whole virus influenza A/H5N1 vaccine given alone or with aluminum hydroxide adjuvant in healthy adults. Vaccine. 2009;27(47):6642-8.
Kitano M et al. Efficacy of single intravenous injection of peramivir against influenza B virus infection in ferrets and cynomolgus macaques. Antimicrobial agents and chemotherapy. 2011;55(11):4961-70.
Konig R et al. Human host factors required for influenza virus replication. Nature. 2010;463(7282):813-7.
Layton RC et al. Delta inulin polysaccharide adjuvant enhances the ability of split-virion H5N1 vaccine to protect against lethal challenge in ferrets. Vaccine. 2011;29(37):6242-51.
Layton RC et al. Enhanced immunogenicity, mortality protection, and reduced viral brain invasion by alum adjuvant with an H5N1 split-virion vaccine in the ferret. PLoS One. 2011;6(6):e20641.
Li CK, et al. Correlates of protection against influenza infection in humans—on the path to a universal vaccine? Current opinion in immunology. 2013;25(4):470-6.
Li J et al Generation of a safe and effective live viral vaccine by virus self-attenuation using species-specific artificial microRNA. J Control Release. 2015;207:70-6.
Li J et al. Intranasal immunization with influenza antigens conjugated with cholera toxin subunit B stimulates broad spectrum immunity against influenza viruses. Human vaccines & immunotherapeutics. 2014;10(5):1211-20.
Li J et al. T-cell-mediated cross-strain protective immunity elicited by prime-boost vaccination with a live attenuated influenza vaccine. International journal of infectious diseases : IJID : official publication of the International Society for Infectious Diseases. 2014;27C:37-43.
Music N et al. Influenza vaccination accelerates recovery of ferrets from lymphopenia. PLoS One. 2014;9(6):e100926.
Noah DL et ak. Qualification of the hemagglutination inhibition assay in support of pandemic influenza vaccine licensure. Clin Vaccine Immunol. 2009;16(4):558-66.
Perez JT et al. MicroRNA-mediated species-specific attenuation of influenza A virus. Nat Biotechnol. 2009;27(6):572-6.
Reed LJ, Muench H. A simple method for estimating fifty percent endpoints. Am J Hyg. 1938;27:493-7.
Rimmelzwaan GF et al. Correlates of protection: novel generations of influenza vaccines. Vaccine. 2008;26 Suppl 4:D41-4.
Rimmelzwaan GF et al. Influenza virus-specific cytotoxic T lymphocytes: a correlate of protection and a basis for vaccine development. Curr Opin Biotechnol. 2007;18(6):529-36.
Rowe T et al. Detection of antibody to avian influenza A (H5N1) virus in human serum by using a combination of serologic assays. J Clin Microbiol. 1999;37(4):937-43.
Sasaki S et al. Influence of prior influenza vaccination on antibody and B-cell responses. PLoS One. 2008;3(8):e2975.
Schmid S, et al. A versatile RNA vector for delivery of coding and noncoding RNAs. J Virol. 2014;88(4):2333-6.
Sridhar S et al. Cellular immune correlates of protection against symptomatic pandemic influenza. Nat Med. 2013;19(10):1305-12.
Thangavel RR et al. Animal models for influenza virus pathogenesis, transmission, and immunology. Journal of immunological methods. 2014.
Wu, Lihong, et al., 'New cross-strain protective influenza vaccine using self-attenuated influenza virus', 2016, Journal of Immunology, vol. 196, Supplement 1.
Yang, Chen, et al. 'Deliberate reduction of hemagglutinin and neuraminidase expression of influenza virus leads to an ultraprotective live vaccine in mice', 2013, Proceedings of the National Academy of Sciences, vol. 110, pp. 9481-9486.
Yen HL et al. Changes in H5N1 influenza virus hemagglutinin receptor binding domain affect systemic spread. Proc Natl Acad Sci U S A. 2009;106(1):286-91.
Yuhas Y et al. Involvement of tumor necrosis factor alpha and interleukin-1beta in enhancement of pentylenetetrazole-induced seizures caused by Shigella dysenteriae. Infect Immun. 1999;67(3):1455-60.

* cited by examiner

SEQUENCE LISTING

<160> NUMBER OF SEQ ID NOS: 8

<210> SEQ ID NO 1
<211> LENGTH: 133
<212> TYPE: DNA
<213> ORGANISM: Artificial Sequence
<220> FEATURE:
<223> OTHER INFORMATION: Synthetic primer

<400> SEQUENCE: 1

```
gttaactccc gtcttggacc tcagtcctgg gggctccaaa gtgctgttcg tgcaggtagt      60

gtgattaccc aacctactgc tgagctagca cttcccgagc ccccgggaca cgttctctct     120

gccaattctc gag                                                        133
```

<210> SEQ ID NO 2
<211> LENGTH: 133
<212> TYPE: DNA
<213> ORGANISM: Artificial Sequence
<220> FEATURE:
<223> OTHER INFORMATION: Synthetic primer

<400> SEQUENCE: 2

```
gttaactccc gtcttggacc tcagtcctgg gggctcactc ctctgcattg tctccgaagt      60

gtgattaccc aaccttggag caatggcaga ggaaaagagc ccccgggaca cgttctctct     120

gccaattctc gag                                                        133
```

<210> SEQ ID NO 3
<211> LENGTH: 121
<212> TYPE: DNA
<213> ORGANISM: Artificial Sequence
<220> FEATURE:
<223> OTHER INFORMATION: Synthetic primer

<400> SEQUENCE: 3

```
tcccgtcttg gacctcagtc ctgggggctc gtgaaatagt acaaggtgca cagtgtgatt      60

acccaacctg gcacttgtag ctatttctgt gagccccgg gacacgttct ctctgccaat     120

t                                                                     121
```

<210> SEQ ID NO 4
<211> LENGTH: 123
<212> TYPE: DNA
<213> ORGANISM: Artificial Sequence
<220> FEATURE:
<223> OTHER INFORMATION: Synthetic primer

<400> SEQUENCE: 4

```
gaaggtatat tgctgttgac agtgagcgac tgtaaacatc ctcgactgga agctgtgaag      60

ccacagatgg gctttcagtc ggatgtttgc agctgcctac tgcctcggac ttcaaggggc     120

tac                                                                   123
```

<210> SEQ ID NO 5
<211> LENGTH: 123

-continued

<212> TYPE: DNA
<213> ORGANISM: Artificial Sequence
<220> FEATURE:
<223> OTHER INFORMATION: Synthetic primer

<400> SEQUENCE: 5
gaaggtatat tgctgttgac agtgagcgac tcccaatgag gtcaaagaga agctgtgaag 60
ccacagatgg gcttctcttt cctcattggg agctgcctac tgcctcggac ttcaaggggc 120
tac 123

<210> SEQ ID NO 6
<211> LENGTH: 123
<212> TYPE: DNA
<213> ORGANISM: Artificial Sequence
<220> FEATURE:
<223> OTHER INFORMATION: Synthetic primer

<400> SEQUENCE: 6
gaaggtatat tgctgttgac agtgagcgac tagaagaatc gtcggttgca ggctgtgaag 60
ccacagatgg gcctgcaacc cgattcttct agctgcctac tgcctcggac ttcaaggggc 120
tac 123

<210> SEQ ID NO 7
<211> LENGTH: 123
<212> TYPE: DNA
<213> ORGANISM: Artificial Sequence
<220> FEATURE:
<223> OTHER INFORMATION: Synthetic primer

<400> SEQUENCE: 7
gaaggtatat tgctgttgac agtgagcgac cacatctggt cttgtttttc tgctgtgaag 60
ccacagatgg gcagaaaaac gaccagatgt ggctgcctac tgcctcggac ttcaaggggc 120
tac 123

<210> SEQ ID NO 8
<211> LENGTH: 123
<212> TYPE: DNA
<213> ORGANISM: Artificial Sequence
<220> FEATURE:
<223> OTHER INFORMATION: Synthetic primer

<400> SEQUENCE: 8
gaaggtatat tgctgttgac agtgagcgac taaggttata gatagctggg agctgtgaag 60
ccacagatgg gctcccagct ctataacctt agctgcctac tgcctcggac ttcaaggggc 120
tac 123

SELF-ATTENUATED PROPHYLACTIC AND THERAPEUTIC VACCINES AGAINST PATHOGENS

CROSS-REFERENCE TO RELATED APPLICATIONS

This application claims priority to, and is the National Stage of International Application No. PCT/US2019/028065, filed on Apr. 18, 2019 and claims priority to U.S. Provisional Application Ser. No. 62/660,327, filed Apr. 20, 2018, the entire contents of each of which are incorporated herein by reference.

STATEMENT OF FEDERALLY FUNDED RESEARCH

This invention was made with government support under R21AI133207 awarded by National Institutes of Health/National Institute of Allergy and Infectious Diseases. The government has certain rights in the invention.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Apr. 17, 2019, is named TECH2120WO_SeqList.txt and is 4, kilobytes in size.

TECHNICAL FIELD OF THE INVENTION

The present invention relates in general to the field of novel, self-attenuated prophylactic and therapeutic vaccines against viral pathogens.

BACKGROUND OF THE INVENTION

Without limiting the scope of the invention, its background is described in connection with therapeutic vaccines.

Influenza is a significant public health problem, despite the heavy campaign for flu vaccination in many countries. Vaccine development against infectious diseases such as influenza is often a challenge because multiple isotypes and strains exist and segment reassortment among them is inevitable. However, antigenic drift (mutation) (caused by the low-fidelity viral polymerase and immunity stress) and antigenic shift (caused by reassortment among multiple subtypes, and also by immunity stress) make influenza vaccination a severe challenge since yearly reformulated influenza vaccines do not always match the circulating strains[6]. Influenza activity in the United States has been significantly increasing since the beginning of November, 2017.

Several influenza activity indicators were higher than is typically seen for this time of year. Influenza activity data from CDC indicate that currently circulating/predominating A(H3N2) viruses are antigenically less similar to egg-grown A(H3N2) viruses used for producing the majority of influenza vaccines in the United States [2]. Although two classes of antiviral compounds, the neuraminidase (NA) blockers (laninamivir, oseltamivir, peramivir, and zanamivir) and the M2 inhibitors (amantadine and rimantadine), are currently approved for the prevention and treatment of influenza, the emergence of drug resistant influenza mutant strains is the greatest challenge [1].

One such patent application is U.S. Patent Publication No. US20170232097A1, filed by the present inventors entitled, "Live Attenuated Viral Vaccine Created by Self-Attenuation With Species-Specific Artificial MicroRNA". This application describes a live attenuated virus and methods of making the same that includes an isolated virus comprising a viral genome that expresses one or more viral antigens; and one or more exogenous species-specific microRNAs inserted into the viral genome that includes a miR-93 backbone-based cassette for species-specific microRNA expression, wherein the species-specific microRNAs are ubiquitously expressed in a viral target species cell but not in a viral propagation cell.

Another such patent is issued U.S. Pat. No. 8,883,995, filed by TenOever, Benjamin, entitled, "Live Attenuated Influenza Virus Vaccines Comprising MicroRNA Response Elements". This patent describes a live attenuated influenza virus (LAIV) vaccine comprising one or more microRNA (miRNA) Response Element(s) (MRE) within an influenza virus genome. The MREs are said to be derived from any miRNA that is highly expressed in influenza-targeted cells of an animal in need of vaccination, but are not expressed or are expressed at very low levels in species (e.g., embryonated chicken eggs) or cell lines used for a large-scale vaccine production. It is said that this design allows for efficient vaccine production but renders the vaccine virus susceptible to attenuation in the influenza-targeted cells of vaccinated animals expressing a cognate miRNA.

Thus, a need remains for novel prophylactic vaccines and therapeutic and treatments that are not circumvented by antigenic drifts and shifts in viral antigen.

SUMMARY OF THE INVENTION

In one embodiment, the present invention includes a live, self-attenuated therapeutic vaccine comprising, consisting essentially of, or consisting of: an isolated virus comprising a viral genome that expresses one or more viral antigens; an artificial microRNA 30 (amiR-30) or other microRNA expression cassette inserted into a viral neuraminidase (NA) or a viral non-structural (NS) gene segment that expresses an amiR-30 or other microRNA that specifically inhibits the expression of a host gene essential for influenza virus replication in host cells; and optionally one or more adjuvants, excipients, or buffers, wherein the therapeutic vaccine is adapted for at least one of: pulmonary, intraalveolar, or nasal administration. In one aspect, the microRNA is not miRNA-93.

In another embodiment, the present invention includes a live, self-attenuated virus comprising, consisting essentially of, or consisting of: an isolated virus comprising a viral genome that expresses one or more viral antigens; and an artificial microRNA 30 (amiR-30) or other microRNA expression cassette inserted into a viral neuraminidase (NA) or a viral non-structural (NS) gene segment that expresses an amiR-30 or other microRNA that specifically inhibits the expression of a host gene essential for influenza virus replication in host cells. In one aspect, the isolated virus further comprises a mammalian-specific artificial microRNA 93 (amiR-93) expression cassette inserted into the viral neuraminidase (NA) or the viral non-structural (NS) gene segment that inhibits viral nucleoprotein (NP) gene expression. In another aspect, the amiR-30 comprises a sequence that targets expression of the host gene in a miR-30 backbone. In another aspect, the host gene is at least one of CDC-Like Kinase 1 (CLK1), SON DNA binding protein (SON), cyclin-dependent kinase inhibitor 1B (Cdkn1b), calcium/calmodulin-dependent protein kinase (CaM kinase) IIbeta (CAMK2B), or vacuolar ATPase (vATPase). In another aspect, the microRNA is not expressed in avian cells. In another aspect, the microRNA comprises a miR-93 backbone-based cassette for species-specific microRNA expression. In another aspect, the virus expresses one or more viral antigens that confer protection against H1N1, pandemic H1N1, and H3N2. In another aspect, the virus is packaged into a vaccine. In another aspect, the virus is adapted for pulmonary, oral, nasal, transcutaneous, or mucosal administration. In another aspect, the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens. In another aspect, the virus is packaged into a vaccine and less than 1,000, 500, 400, 300, 200, 100, 90, 80, 70, 60, 50, 40, 30, 20, 10 or 1 viral particle(s) confer protective immunity to the virus. In another aspect, the mature miR-93 loop is replaced with sequence within the mature miR-93 loop was replaced with the sequences at set forth in Table 1. In another aspect, the virus has an $EID_{50}$ of 10 or less. In another aspect, the virus comprises multiple artificial miRNA expression cassettes. In another aspect, the virus is selected from an influenza, human immunodeficiency virus (HIV), hepatitis B virus (HBV), West Nile virus, Dengue Fever, or Zika virus. In another aspect, the virus is adapted for use as a vaccine for prevention of infectious diseases or as therapeutic for post infection treatment. In one aspect, the microRNA is not miRNA-93.

In yet another embodiment, the present invention includes a method of making a live, self-attenuated virus comprising, consisting essentially of, or consisting of: obtaining isolated virus comprising a viral genome that expresses one or more viral antigens; and an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells. In one aspect, the isolated virus further comprises a mammalian-specific artificial microRNA 93 (amiR-93) expression cassette inserted into the viral neuraminidase (NA) or the viral non-structural (NS) gene segment that inhibits viral nucleoprotein (NP) gene expression. In another aspect, the amiR-30 comprises a sequence that targets expression of the host gene in a miR-30 backbone. In another aspect, the host gene is at least one of CDC-Like Kinase 1 (CLK1), SON DNA binding protein (SON), cyclin-dependent kinase inhibitor 1B (Cdkn1b), calcium/calmodulin-dependent protein kinase (CaM kinase) IIbeta (CAMK2B), or vacuolar ATPase (vATPase). In another aspect, the microRNA is not expressed in avian cells. In another aspect, the microRNA comprises a miR-93 backbone-based cassette for species-specific microRNA expression. In another aspect, the virus expresses one or more viral antigens that confer protection against H1N1, pandemic H1N1, and H3N2. In another aspect, the virus is packaged into a vaccine. In another aspect, the virus is adapted for pulmonary, oral, nasal, transcutaneous, or mucosal administration. In another aspect, the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens. In another aspect, the virus is packaged into a vaccine and less than 1,000, 500, 400, 300, 200, 100, 90, 80, 70, 60, 50, 40, 30, 20, 10 or 1 viral particle(s) confer protective immunity to the virus. In another aspect, the mature miR-93 loop is replaced with sequence within the mature miR-93 loop was replaced with the sequences at set forth in Table 1. In another aspect, the virus has an $EID_{50}$ of 10 or less. In another aspect, the virus comprises multiple artificial miRNA expression cassettes. In another aspect, the virus is selected from an influenza, human immunodeficiency virus (HIV), hepatitis B virus (HBV), West Nile virus, Dengue Fever, or Zika virus. In another aspect, the virus is adapted for use as a vaccine for prevention of infectious diseases or as therapeutic for post infection treatment. In one aspect, the microRNA is not miRNA-93.

A method of testing a live, self-attenuated virus for making a vaccine comprising, consisting essentially of, or consisting of: selecting a cell for propagation of a virus that does not express a specific miRNA; obtaining an isolated virus comprising a viral genome that expresses one or more viral antigens; inserting into the viral genome an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells; and determining if the virus propagates in the viral propagation cell but is attenuated in the viral target species cell. In one aspect, the microRNA is not miRNA-93.

In yet another embodiment, the present invention includes a method of treating a patient with a therapeutic vaccine comprising, consisting essentially of, or consisting of: identifying that the patient is in need of prophylaxis or treatment of an active viral infection; and providing the patient with a vaccine comprising a live, attenuated virus that comprises an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells, in an amount effective to provide prophylaxis against, or treatment of, an active viral infection. In one aspect, the isolated virus further comprises a mammalian-specific artificial microRNA 93 (amiR-93) expression cassette inserted into the viral neuraminidase (NA) or the viral non-structural (NS) gene segment that inhibits viral nucleoprotein (NP) gene expression. In another aspect, the amiR-30 comprises a sequence that targets expression of the host gene in a miR-30 backbone. In another aspect, the host gene is at least one of CDC-Like Kinase 1 (CLK1), SON DNA binding protein (SON), cyclin-dependent kinase inhibitor 1B (Cdkn1b), calcium/calmodulin-dependent protein kinase (CaM kinase) IIbeta (CAMK2B), or vacuolar ATPase (vATPase). In another aspect, the microRNA is not expressed in avian cells. In another aspect, the microRNA comprises a miR-93 backbone-based cassette for species-specific microRNA expression. In another aspect, the virus expresses one or more viral antigens that confer protection against H1N1, pandemic H1N1, and H3N2. In another aspect, the virus is packaged into a vaccine. In another aspect, the virus is adapted for pulmonary, oral, nasal, transcutaneous, or mucosal administration. In another aspect, the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens. In another aspect, the virus is packaged into a vaccine and less than 1,000, 500, 400, 300, 200, 100, 90, 80, 70, 60, 50, 40, 30, 20, 10 or 1 viral particle(s) confer protective immunity to the virus. In another aspect, the mature miR-93 loop is replaced with sequence within the mature miR-93 loop was replaced with the sequences at set forth in Table 1. In another aspect, the virus has an $EID_{50}$ of 10 or less. In another aspect, the virus comprises multiple artificial miRNA expression cassettes. In another aspect, the virus is selected from an influenza, human immunodeficiency virus (HIV), hepatitis B virus (HBV), West Nile virus, Dengue Fever, or Zika virus. In another aspect, the virus is adapted for use as a vaccine for prevention of infectious diseases or as therapeutic for post infection treatment. In one aspect, the microRNA is not miRNA-93.

BRIEF DESCRIPTION OF THE DRAWINGS

For a more complete understanding of the features and advantages of the present invention, reference is now made to the detailed description of the invention along with the accompanying figures and in which:

(FIG. 2A) Diagrams of engineered and original NA gene segments. Blue represents 5' and 3' non-coding regions; green represents packaging signal within open reading frame; red represents NA coding sequence. (Top) Organization of original NA gene segment. (Bottom) Organization of modified NA gene segment engineered with miR-30 or amiR-30CLK1 expression cassettes. (FIG. 2B) RNA was isolated from purified PR8, PR8-miR-30 or PR8-amiR-30CLK1, and 1 μg RNA was separated on a 4% acrylamide TBE urea gel for silver staining. Each RNA segment is labeled to the right of the gel. (FIG. 2C) M and NA gene segments were amplified by RT-PCR and separated by electrophoresis on agarose gel.

(FIG. 3A) MEF cells were infected with different influenza viruses, and then harvested at 48 hours post-infection. CLK1 proteins were analyzed by Western-blot. (FIG. 3B) A549 cells were infected with different influenza viruses, and then harvested at 48 hours post-infection. CLK1 proteins were analyzed by Western-blot. (FIG. 3C) MEF cells were infected with different influenza viruses, and then RNA was isolated at 48 h post transfection. CLK1 were amplified by RT-PCR and separated by electrophoresis on agarose gel. (FIG. 3D) A549 cells were infected with different influenza viruses, and then RNA was isolated at 48 h post transfection. CLK1 were amplified by RT-PCR and separated by electrophoresis on agarose gel.

DETAILED DESCRIPTION OF THE INVENTION

Figure 1A:
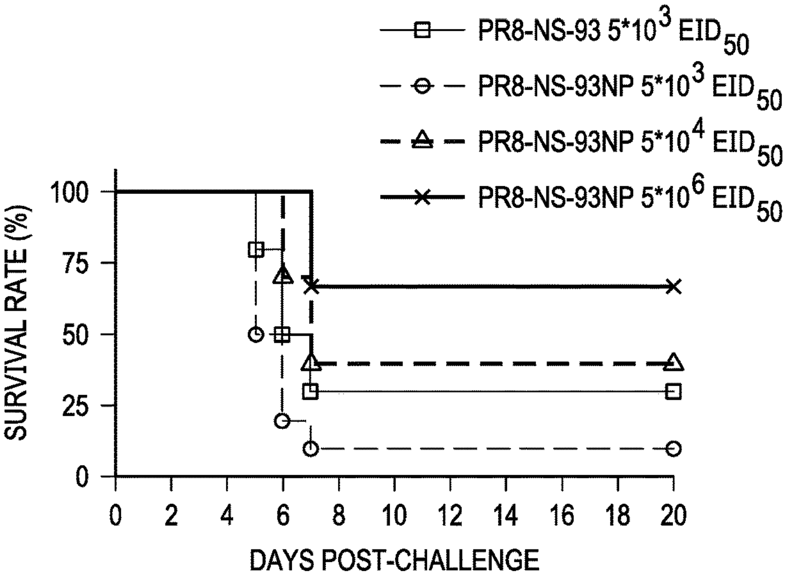
FIGS. 1A and 1B show the testing of therapeutic effects of viral gene NP-targeted SAIV, PR8-NS-amiR-93NP. 6-8 week old Balb/C mice (10/group, 5 male and 5 female) were first intranasally infected with 20×MLD50 ($10^4$ PFU) of homologous wild-type H1N1 PR8 influenza virus, and 6 hours later, they were intranasally inoculated with $5\times10^3$-$5\times10^5$ EID50 control PR8-NS-93 or SAIV PR8-NS-amiR-93NP, or with $5\times10^3$ EID50 control PR8-NS-93 viruses. Mouse weight changes and death were recorded for 21 days (FIG. 1A); Survived mice from experiment groups in Panel A were then infected intranasally with $10^4$ PFU of heterologous H3N2 HK68 influenza virus (FIG. 1B). Another group of naive mice (without pre-exposure to influenza virus) were inoculated with HK68 influenza virus as the control group. Infected mice were euthanized at different time points to collect lungs and determined virus titers by plaque assay (FIG. 1B).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

This invention describes a new class of prophylactic and therapeutic vaccine against microbial pathogen-caused infectious diseases such as influenza. The vaccine is live attenuated vaccine created by pathogen self-attenuation mechanism. The invention has been tested with the model of influenza virus and mouse model of influenza infection. Using reverse genetics technology, the inventors have previously constructed a new class of live attenuated influenza virus (LAIV) and the inventors also named them as self-attenuated influenza virus (SAIV), which carries a mammalian-specific artificial microRNA-93 (amiR-93) expression cassette in its NS gene segment and expresses an amiR-93 that inhibits the essential viral NP gene expression. In the present invention, the SAIV carries an unrelated microRNA, namely, an artificial microRNA 30 (amiR-30) expression cassette in its NA gene segment and expresses an amiR-30 that can specifically inhibit the expression of a host gene, such as Cdc2-like kinase 1 (CLK1), which is essential for influenza virus replication in host cells. The inventors demonstrated that a single dose intranasal vaccination with any one of the two resultant SAIVs: NP-targeted SAIV, PR8-NS-amiR-93NP and CLK1-targeted SAIV, PR8-NA-amiR-30CLK1) provided potent immune protection against challenge with lethal dose of influenza A virus. Additionally, administration of these SAIV 6 hours post lethal influenza infection could significantly protect mice against influenza. Therefore, this new type of SAIV vaccine can be used as a prophylactic vaccine and anti-influenza drug for post-exposure treatment. It will also prevent the treated subjects from possible future influenza infection. Additionally, the inventors developed a dual-targeted SAIV that can express both anti-NP amiR-93 and anti-CLK1 amiR-30 to inhibit the expression of both viral NP and the host CLK1 genes. Such dual-targeted SAIV (Named PR8-NS-amiR93-NP/NA-amiR30-CLK1) provides synergistic effect on protection against broad-spectrum influenza viruses. The broader applicability of the invention will be the creation of prophylactic and therapeutic vaccines against many infectious diseases, caused by microbial pathogens such as HIV, HBV, Zika viruses, and even microbes such as *Mycobacterium tuberculosis*, etc.

A dosage unit for use of the self-attenuated prophylactic and therapeutic vaccines of the present invention may be a single compound or mixtures thereof with other compounds. The compounds may be mixed together, form ionic or even covalent bonds. The self-attenuated prophylactic and therapeutic vaccines of the present invention may be administered in oral, pulmonary, nasal, transcutaneous, mucosal, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., inhalers, suspensions, and emulsions may be used to provide the self-attenuated prophylactic and therapeutic vaccines of the present invention to a patient in need of therapy that includes the self-attenuated prophylactic and therapeutic vaccines. The self-attenuated prophylactic and therapeutic vaccines may also be administered as any one of known salt forms.

The self-attenuated prophylactic and therapeutic vaccines are typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the self-attenuated prophylactic and therapeutic vaccines may be formulated to provide, e.g., maximum and/or consistent dosing for the particular form for oral, rectal, topical, intravenous injection or parenteral administration. While the self-attenuated prophylactic and therapeutic vaccines may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

The self-attenuated prophylactic and therapeutic vaccines may be administered in the form of liposome delivery systems, e.g., small unilamellar vesicles, large unilamellar vesicles, and multilamellar vesicles, whether charged or uncharged. Liposomes may include one or more: phospholipids (e.g., cholesterol), stearylamine and/or phosphatidylcholines, mixtures thereof, and the like.

The self-attenuated prophylactic and therapeutic vaccines may also be coupled to one or more soluble, biodegradable, bioacceptable polymers as drug carriers or as a prodrug. Such polymers may include, for example: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the self-attenuated prophylactic and therapeutic vaccines may be coupled one or more biodegradable polymers to achieve controlled release of the self-attenuated prophylactic and therapeutic vaccines, biodegradable polymers for use with the present invention include: polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

For direct delivery to the nasal passages, sinuses, mouth, throat, esophagus, trachea, lungs and alveoli, the self-attenuated prophylactic and therapeutic vaccines may also be delivered as an intranasal form via use of a suitable intranasal vehicle. For dermal and transdermal delivery, the self-attenuated prophylactic and therapeutic vaccines may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of self-attenuated prophylactic and therapeutic vaccines may include the following forms.

The present invention provides new solutions to prevent and treat microbial infections. This new class of therapeutic vaccine is live attenuated vaccine, it mimic the pathogen's natural infection and has potential to elicited more potent both antibody and cellular immune responses. This may lead to cross-strain protective immunity. The vaccine may not need to be reformulated every year. The pathogen is attenuated by down-regulation of either pathogen or/and host gene expression, changes (such of mutations) of microbial strains will not affect the effectiveness of the attenuation or the efficacy of the post-exposure treatment. This will avoid the emergence of drug resistance. Finally, patients recovered from treatment of the therapeutic vaccine with acquired immunity and are protected against possible future viral infection by the same pathogen.

This is a new antibiotic-independent approach to prevent and treat infectious diseases. Previously, live attenuated vaccines are created by mutations/deletions of pathogen components. There is a potential to have reverse mutations that may lead to occurrence of pathogenic microbial strains. The invention provides a completely new class of vaccine and treatment against influenza and other infectious diseases caused by microbial infection. The therapeutic vaccine disclosed herein is a live, attenuated vaccine created by targeting pathogen and/or host gene expression through self-attenuation. By insertion of an artificial microRNA 30 (amiR-30) and/or a mammalian-specific artificial miR-93 (amiR-93) expression system into microbial genome, this will itself attenuate the pathogen. Moreover, as a post-exposure therapy, the therapeutic live attenuated virus will only specifically target the host cells, which have specific receptors, involved in the pathogenesis. This design avoids any possible side effects on other cells not involved in the pathogenesis.

The inventors self-attenuated influenza virus (SAIV) technology was used for construction of recombinant influenza virus vaccine by targeting a host cell gene/factor, instead of viral gene (pathogen). Recent research by genome-wide RNA interference (RNAi) has identified some host genes critical for influenza virus replication after entry into host cells [4, 5]. Therefore, the inventors targeted silencing of these host genes to inhibit or reduce influenza virus replication and therefore therapeutic effects against influenza virus infection. Infection with this type of SAIV can also induce protective immune responses and prevent future re-infection by other influenza virus strains. The inventors successfully constructed an SAIV, PR8-NA-amiR-CLK1, expressing an artificial microRNA that inhibits expression of host cell Cdc2-like kinase 1 (CLK1), which has been shown to be important for influenza virus replication in the host [4, 5]. These studies show that the SAIV, PR8-NA-amiR-CLK1, is feasible to be used as a prophylactic and therapeutic vaccine in mouse model of influenza infection (FIGS. 4A-D and 5A-5B).

Production and evaluation of dual viral and host factor-targeted prophylactic and therapeutic SAIV vaccine. A dual-targeted live attenuated influenza virus can also be used as a safe and broad spectrum treatment against influenza viruses. A dual-targeted SAIV expresses two amiRNA in two influenza viral segments (NS and NA), which can silence one viral NP gene and one host CLK1 gene. This strategy minimizes the risk of reverse mutations and provides a synergistic effect on protection against influenza.

A novel platform technology was used to create live attenuated influenza virus vaccine using self-attenuation mechanism mediated by artificial microRNAs. MicroRNA (miRNA) are non-coding endogenous RNAs that direct post-transcription regulation of gene expression by interacting with messenger RNAs and targeting them for degradation or reduction of coding capacity. miRNA-based gene silencing is hence a promising approach to control viral replication and may be used to improve the safety of attenuated live vaccine. Recent studies showed that many miRNA are species- and tissue-specific [3-5]. These characters of miRNA can be used to modify the replicative tropism of RNA and DNA viruses [6-9]. A number of studies have inserted miRNA targeted sequence into some viral genomes for successful RNAi [5, 10, 11]. With the advance of influenza reverse genetics and miRNA molecular biology, using influenza virus as the vector to deliver amiRNA is now feasible [10]. Although miRNA are evolutionarily conserved, a small number of miRNA are species-specific, such as miR-93, which is not present in avian cells [11]. In this research, the inventors developed a novel SAIV expressing a functional mammalian species-specific amiRNA that also inhibits conserved viral gene NP for influenza virus production. The resulting live attenuated influenza virus can produce inhibitory amiRNA to silence the conserved target expression only in mammalian cells, but not in avian cells. Therefore, the engineered influenza virus can be productively produced with commercially viable way using embryonated chicken eggs, but replication-deficient in mammalian cells [3]. Additionally, the SAIV expressing amiRNA inhibits expression of host cell Cdc2-like kinase 1 (CLK1), which has been shown to be important for influenza virus replication in the host cells [4]. This dual-targeting approach against both viral and host factors provide synergistic or additive effects of antiviral and protective responses with higher safety profile.

Intranasal delivery of the proposed SAIV is target-specific treatment that can avoid side-effects from traditionally systemic administration of antiviral drugs. For influenza virus that targets the respiratory system, intranasal delivery of the proposed therapeutics is an ideal strategy to specifically target influenza virus-infected cells, such as epithelial cells in the lung. This further limits any potential side effects that may affect other types of cells and organs not involved in influenza pathogenesis.

Novel therapeutic vaccine against influenza. The present inventors engineered an influenza virus, SAIV, as an effective countermeasure against influenza. Intranasal administration of the proposed SAIV therapeutic virus mimics the natural influenza virus infection. Host protective immunity is ignited and amplified against future re-infection while the SAIV are truly attenuated through producing inhibitory amiR against viral or/and host factor (s) essential for influenza virus replication and propagation. Therefore, the SAIV can be used as a therapeutic vaccine to treat influenza infection and prevent future re-infection.

A model SAIV was made using species-specific amiRNA. The inventors designed an amiR-93 cassette for insertion into NS gene segment of the genome of influenza virus PR8 (H1N1), which produces an amiRNA specific for silencing NP gene expression. The resultant virus, PR8-NS-amiR-93NP, is replication-deficient in mammalian cells, but could be propagated in chicken eggs at high titers. This SAIV was significantly attenuated by 10,000 fold in mice compared with its wild-type counterpart, influenza PR8 virus. In animal experiments, a single-dose intranasal vaccination with this novel SAIV virus (PR8-NS-amiR-93NP) provides potent and cross-strain immune protection against challenge with lethal influenza virus infection, including homologous PR8 influenza virus, heterologous HK68 H3N2 influenza virus and CA09 H1N1 pandemic influenza virus [3].

Figure 1B:
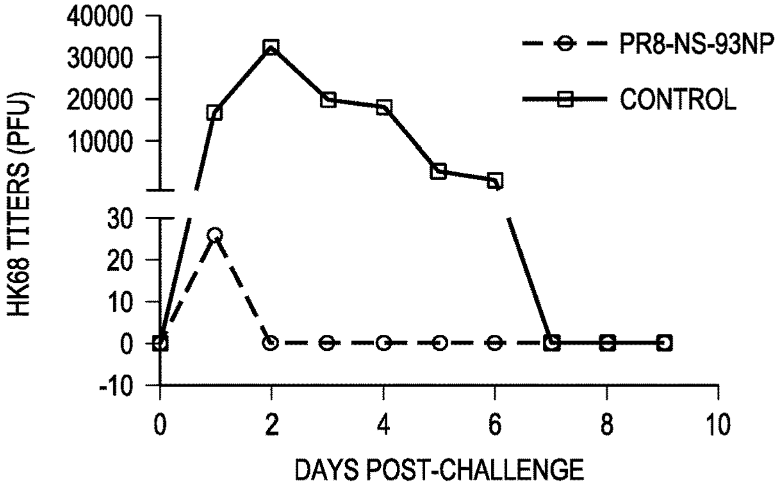
Figure 2A:
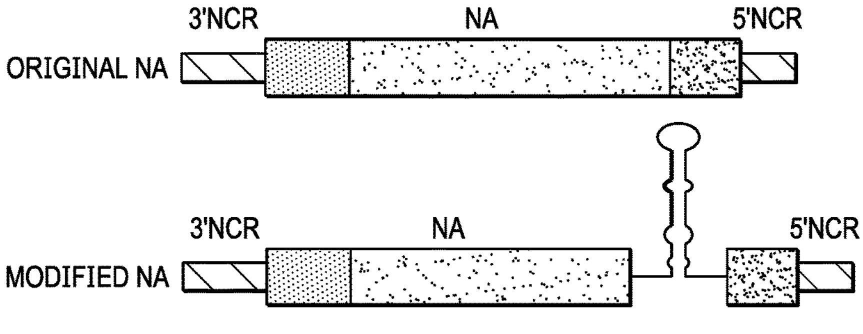
FIGS. 2A to 2C show the engineering of NA gene segment and verification of rescued host gene CLK1-targeted influenza virus.
Figure 2B:
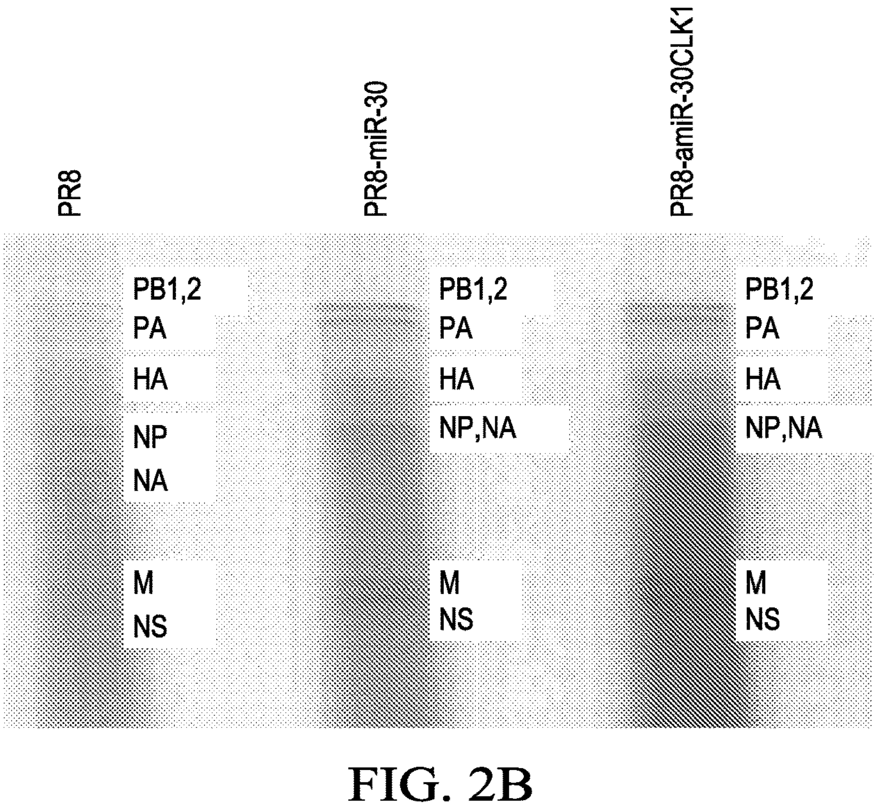
Figure 2C:
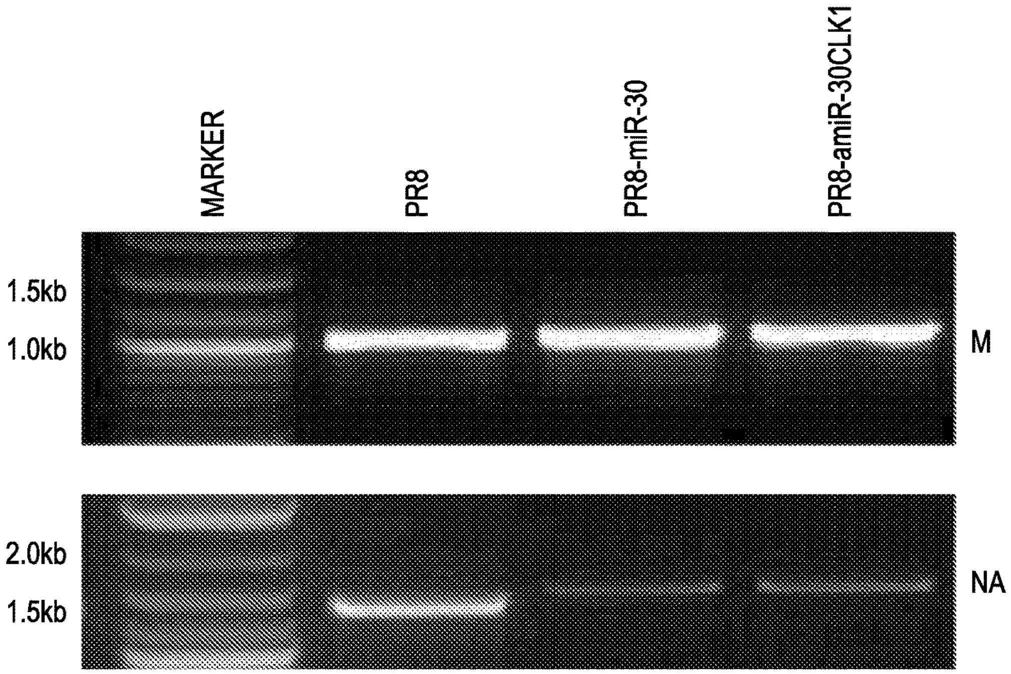
Figure 3C:
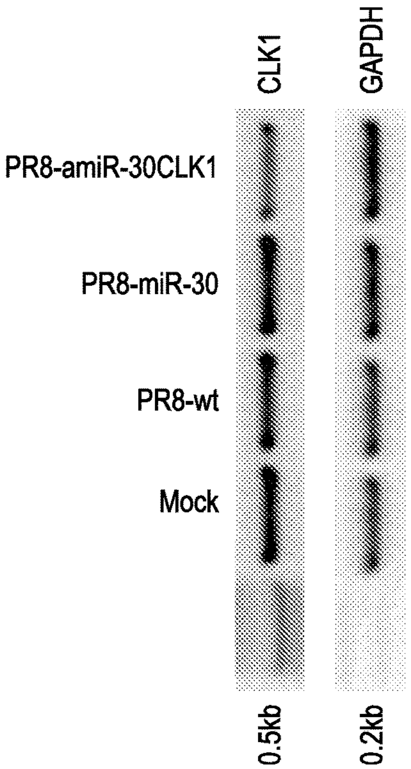
FIGS. 3A to 3D show the replication of wild-type and host CLK1-targetted SAIV, PR8-NA-amiR-30CLK1.
Figure 3D:
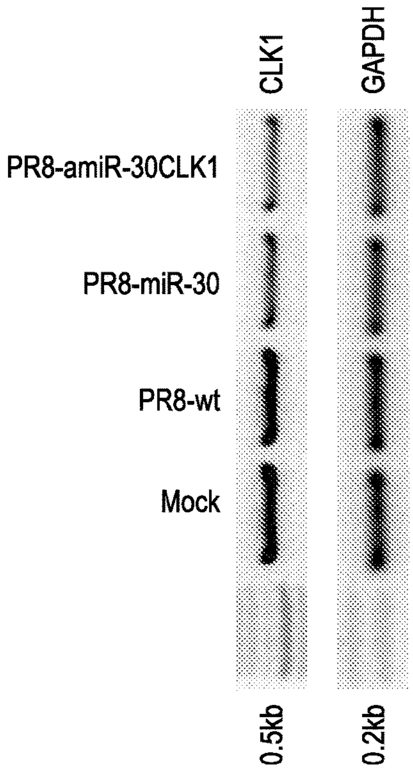
Figure 3A:
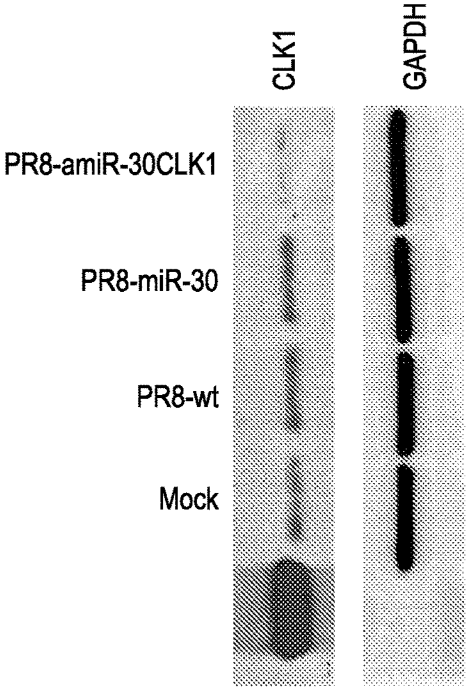
Figure 3B:
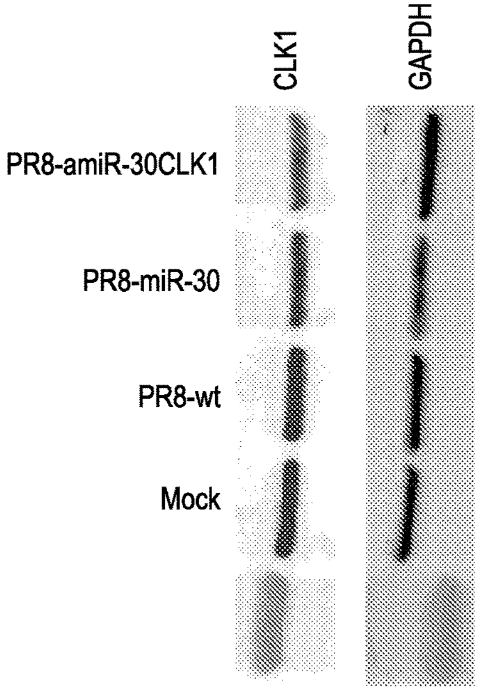
Figure 4A:
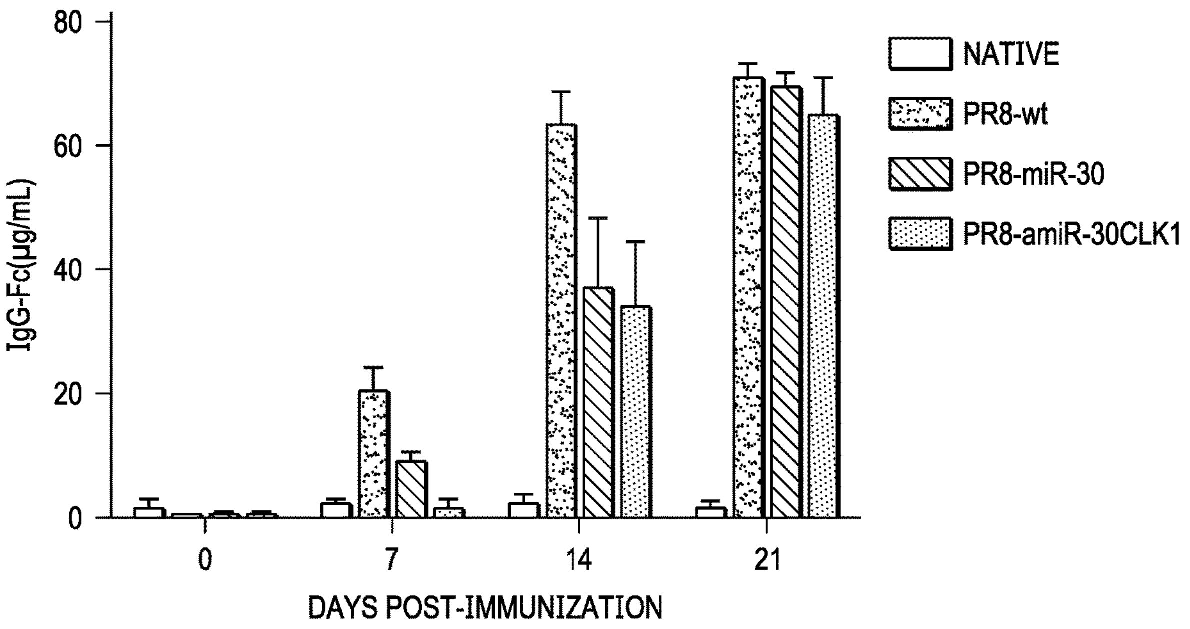
FIGS. 4A to 4D show the protective immune responses induced by host CLK1-targetted SAIV, PR8-NA-amiR-30CLK1 in mice. Balb/c mice (n=10) were intranasally vaccinated with PR8-NA-amiR-30CLK1 and control PR8 viruses on day 0 and blood were collected at days 0, 7, 14, and 21 post-vaccination. At 21 days post-vaccination, Mice (n=10) were challenged with 50×MLD50 wild type PR8 virus. HA-specific antibodies IgG (FIG. 4A) and IgG1 (FIG. 4B) were measured by ELISA. Mouse weight changes (FIG. 4C) and survival rate (FIG. 4D) after viral challenge are shown.
Figure 4B:
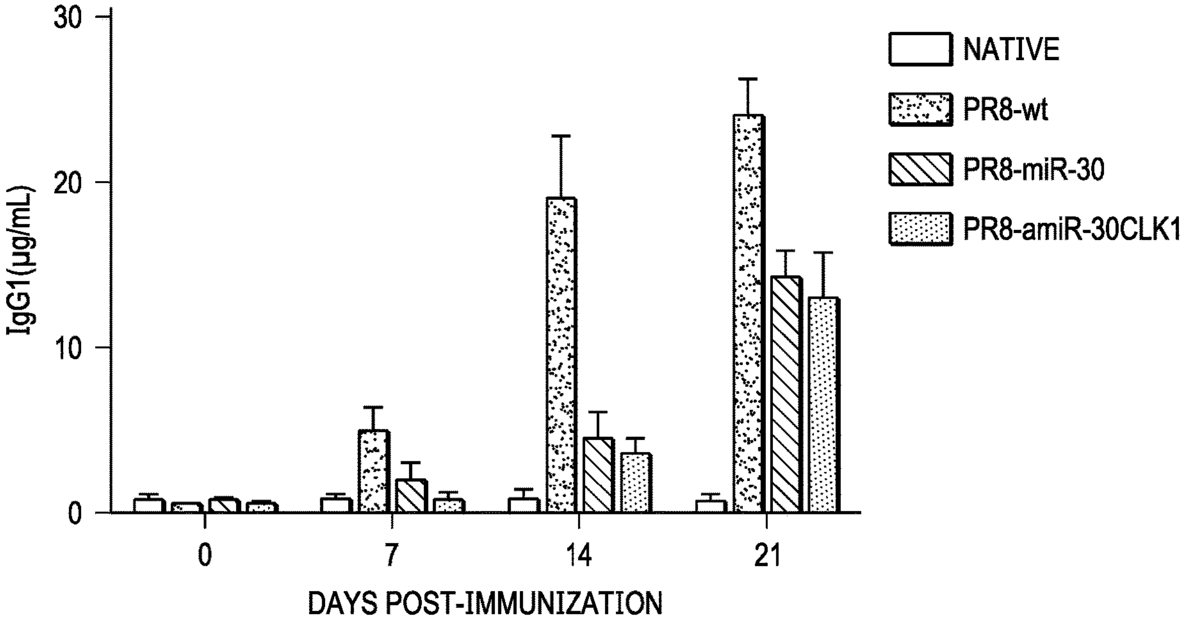
Figure 4C:
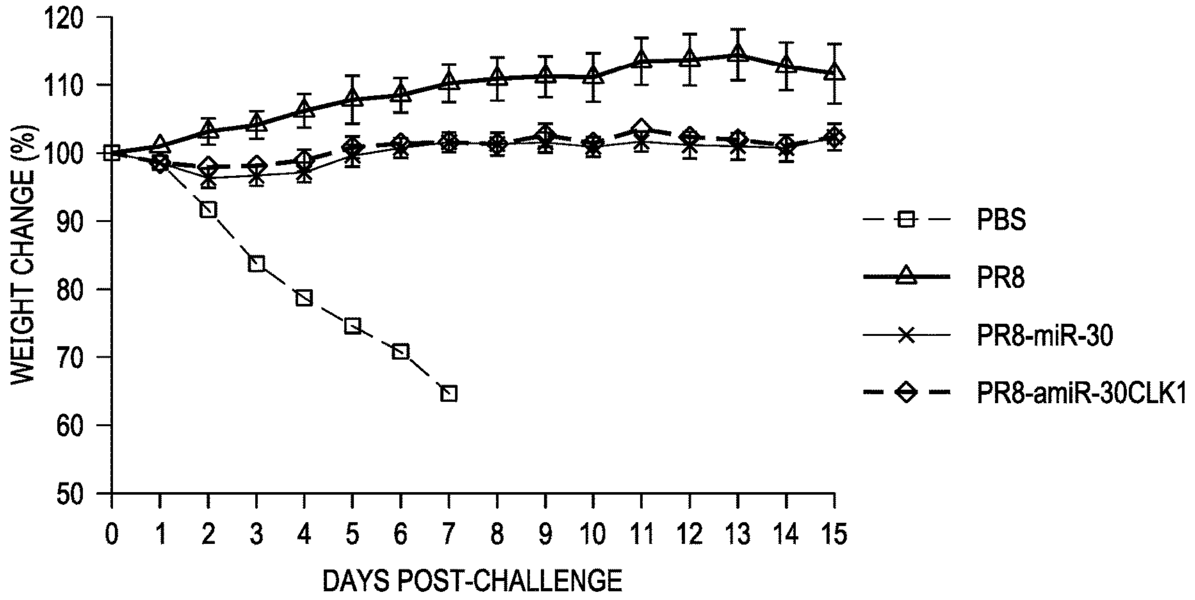
Figure 4D:
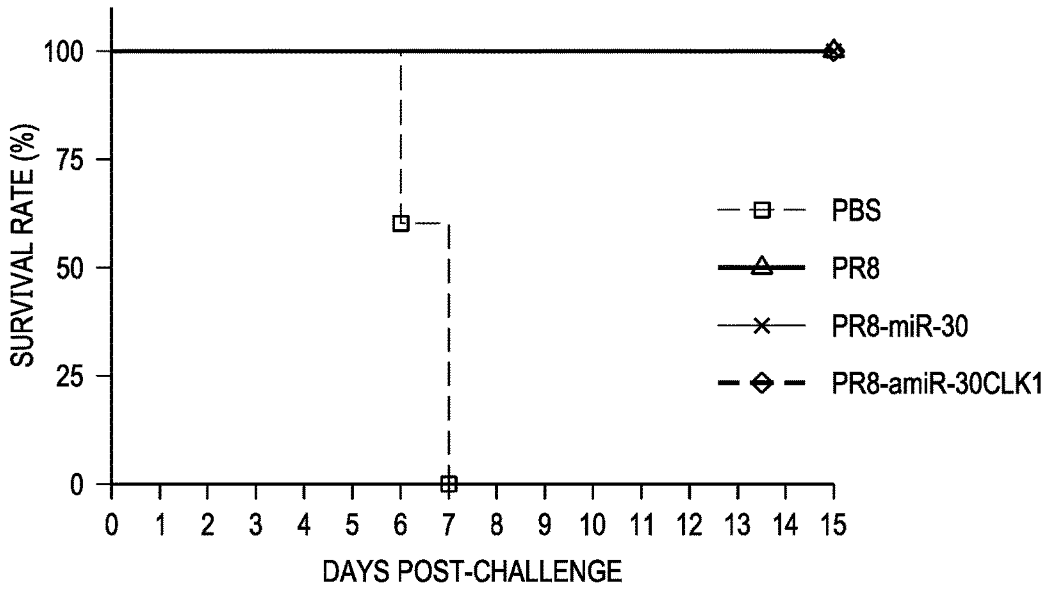

Additionally, the inventors performed experiments to show if viral gene NP targeted SAIV, PR8-NS-amiR-93NP, could be used as anti-influenza therapy and therapeutic vaccine for post-exposure treatment. Groups of 6-8 week old Balb/C mice (10/group, 5 male and 5 female) were first intranasally infected with lethal dose of wild-type PR8 influenza virus, and 6 hours later, they were intranasally inoculated with $5\times10^3$-$5\times10^5$ $EID_{50}$ control PR8-NS-93 or SAIV PR8-NS-amiR-93NP. FIG. 1A shows that the $5\times10^5$ $EID_{50}$ dose of SAIV treatment has significant higher survival rate than the control PR8-NS-93 group ($P<0.05$). Interestingly, survived mice from PR8-NS-amiR-93NP treatment were further protected against heterologous H3N2 HK68 influenza virus infection (FIG. 1B). These data demonstrate that the viral gene targeted SAIV, PR8-NS-amiR-93NP, can be used as an effective treatment and therapeutic vaccine against influenza virus infection. Table 1 includes a list of original and artificial MicroRNA (amiR) sequences for use with the present invention.

TABLE 1

| List of Original and Artificial MicroRNA (amiR) Sequences: |
|---|
| (1) Original MicroRNA 93 (miR-93)<br>GTTAACTCCCGTCTTGGACCTCAGTCCTGGGGGCTC**CAAAGTGCTGTTC**<br>**GTGCAGGTAG**TGTGATTACCCAACCT**ACTGCTGAGCTAGCACTTCCCG**A<br>GCCCCCGGGACACGTTCTCTCTGCCAATTCTCGAG (SEQ ID<br>NO: 1) |
| (2) amiR-93-NP<br>GTTAACTCCCGTCTTGGACCTCAGTCCTGGGGGCTC**ACTCCTCTGCATT**<br>**GTCTCCGAAG**TGTGATTACCCAACCT**TGGAGCAATGGCAGAGGAAAAG**A<br>GCCCCCGGGACACGTTCTCTCTGCCAATTCTCGAG (SEQ ID<br>NO: 2) |
| (3) amiR-93-SON<br>TCCCGTCTTGGACCTCAGTCCTGGGGGCTC**GTGAAATAGTACAAGGTGC**<br>**ACAG**TGTGATTACCCAACCT**GGCACTTGTAGCTATTTCTGTG**AGCCCCC<br>GGGACACGTTCTCTCTGCCAATT (SEQ ID NO: 3) |
| (4) Original MicroRNA-30 (miR-30)<br>GAAGGTATATTGCTGTTGACAGTGAGCGAC**TGTAAACATCCTCGACTGG**<br>**AAG**CTGTGAAGCCACAGATGGG**CTTTCAGTCGGATGTTTGCAGC**TGCCT<br>ACTGCCTCGGACTTCAAGGGGCTAC (SEQ ID NO: 4) |
| (5) amiR-30-CLK1<br>GAAGGTATATTGCTGTTGACAGTGAGCGAC**TCCCAATGAGGTCAAAGAG**<br>**AAG**CTGTGAAGCCACAGATGGG**CTTCTCTTTCCTCATTGGGAGC**TGCCT<br>ACTGCCTCGGACTTCAAGGGGCTAC (SEQ ID NO: 5) |
| (6) amiR-30-Cdkn1b<br>GAAGGTATATTGCTGTTGACAGTGAGCGAC**TAGAAGAATCGTCGGTTGC**<br>**AGG**CTGTGAAGCCACAGATGGG**CCTGCAACCCGATTCTTCTAGC**TGCCT<br>ACTGCCTCGGACTTCAAGGGGCTAC (SEQ ID NO: 6) |
| (7) amiR-30-CAMK2B<br>GAAGGTATATTGCTGTTGACAGTGAGCGAC**CACATCTGGTCTTGTTTTT**<br>**CTG**CTGTGAAGCCACAGATGGG**CAGAAAAACGACCAGATGTGGC**TGCCT<br>ACTGCCTCGGACTTCAAGGGGCTAC (SEQ ID NO: 7) |
| (8) amiR-30-vATPase (ATP6V0C)<br>GAAGGTATATTGCTGTTGACAGTGAGCGAC**TAAGGTTATAGATAGCTGG**<br>**GAG**CTGTGAAGCCACAGATGGG**CTCCCAGCTCTATAACCTTAGC**TGCCT<br>ACTGCCTCGGACTTCAAGGGGCTAC (SEQ ID NO: 8) |

Note:
Gene targeting sequences are marked in bold.

Evaluation of the therapeutic efficacy by the viral gene-targeted SAIV in mice. Groups of mice (10/group, 5 male and 5 female) will be first intranasally inoculated with $10$-$10^2\times MLD_{50}$ mouse adapted CA09 H1N1 virus. One day later, they will be nasally administered with $10^2$-$10^4\times EID_{50}$ our viral gene-targeted SAIV, PR8-NS-amiR-93NP. For positive control group, mice will be treated with anti-influenza virus drugs such as oseltamivir or zanamivir; additional treatment control group will include mice intranasally inoculated with the licensed LAIV, FluMist (10 µl/mouse). Mouse weight change and survival rates are closely monitored for at least 3 weeks. Additionally, other mouse adapted influenza viruses such as H1N1 A/PR/8/34, H1N1 A/WSN/33 and H3N2 A/Hong Kong/1/1968 (HK68), are used.

Effect of preexisting immunity to the strain subtype of dual targeted SAIV on its therapeutic efficacy: Additionally, using the present invention it is possible to investigate the possibility that pre-existing immunity to the same subtype of our SAIV may interfere with the efficacy of dual-targeted SAIV-based therapy. Animals are pre-exposed to wild type PR8 virus by intranasal inoculation at a dosage of 25 PFU/mouse in 50 µl PBS [12] four weeks before infection with CA09 H1N1 virus and subsequent treatment with the SAIV viruses as above-described.

Efficacy of the viral NP-targeted SAIV as a therapeutic vaccine against influenza. Groups of mice (10/group, 5 male and 5 female) are first intranasally infected with $10$-$10^2\times MLD_{50}$ mouse adapted CA09 H1N1 virus. One day later, they are nasally administered $10^2$-$10^4\times EID_{50}$ SAIV virus selected above (PR8-NS-amiR-93NP). Additional 2 doses of SAIV virus will also be administered on day 3 and 5. Mouse weight change and survival rates are closely monitored for at least 3 weeks. Mouse groups survived from influenza infection/SAIV treatment will be further analyzed for anti-influenza antibody response in the next section. One month later, fully recovered mice are re-challenged intranasally with lethal doses of heterologous influenza viruses, such as H1N1 A/WSN/33 and H3N2 A/Hong Kong/1/1968 (HK68). Mouse weight change and survival rates are closely monitored for at least 3 weeks.

Evaluation of the viral NP-targeted SAIV as a post exposure treatment and therapeutic vaccine in ferrets against influenza. Unlike mice, ferrets are naturally susceptible to unadapted human influenza virus isolates, including influenza A and B strains [13, 14]. Therefore, ferret model of influenza infection resembles closely to human influenza. Selected SAIV treatment protocol with mice will be used in the following studies in ferrets. Groups of ferrets (n=7) (similar design as for mice experiment) will be first intranasally inoculated with $1\times10^6$ PFU of H1N1 CA09 virus. One day later, they will be nasally administered with $10^2$-$10^5\times EID_{50}$ selected SAIV virus PR8-NS-amiR-93NP. For positive control group, ferrets will be administered with anti-influenza virus drugs such as oseltamivir or zanamivir. Animals will be monitored daily for weight loss, clinical illness (i.e., inactivity, lethargy, sneezing, nasal discharge, and hunched back), and body temperature change. To monitor virus replication in nasal cavities, nasal washes will be collected on days 1 to 4 post treatment [15]. Viral titers will be determined as described above [12, 16]. Blood sample will be collected from recovered animals and be used for determining anti-influenza antibody titers and microneutralization titer as described in above sections. One month later, the recovered ferrets will be re-challenged with $1\times10^6$ PFU of a heterologous H3N2 virus A/Victoria/361/2011 (Vic/11). Again, nasal washes will be collected for viral titer analysis on days 1 to 4 post infection. Ferrets will be monitored daily for weight loss, clinical illness, and body temperature change for at least 4 weeks.

Using the similar technology for construction of viral NP-targeted SAIV [3], the inventors produced a new host Cdc2-like kinase 1 (CLK1)-targeted SAIV, PR8-NA-amiR-30CLK1, which has a mi-30 backbone, but targets host CLK1. The inventors designed an artificial miR-30 (amiR-30) cassette for insertion into NA gene segment of the genome of influenza virus PR8 (H1N1), which produces an amiRNA specific for silencing mouse/ferret/human CLK1 gene expression. The correct production of PR8-NA-amiR- 30CLK1 and control virus PR8-miR-30 have been verified in experiments described in FIGS. 2A to 2C and FIGS. 3A to 3D.

Figure 5A:
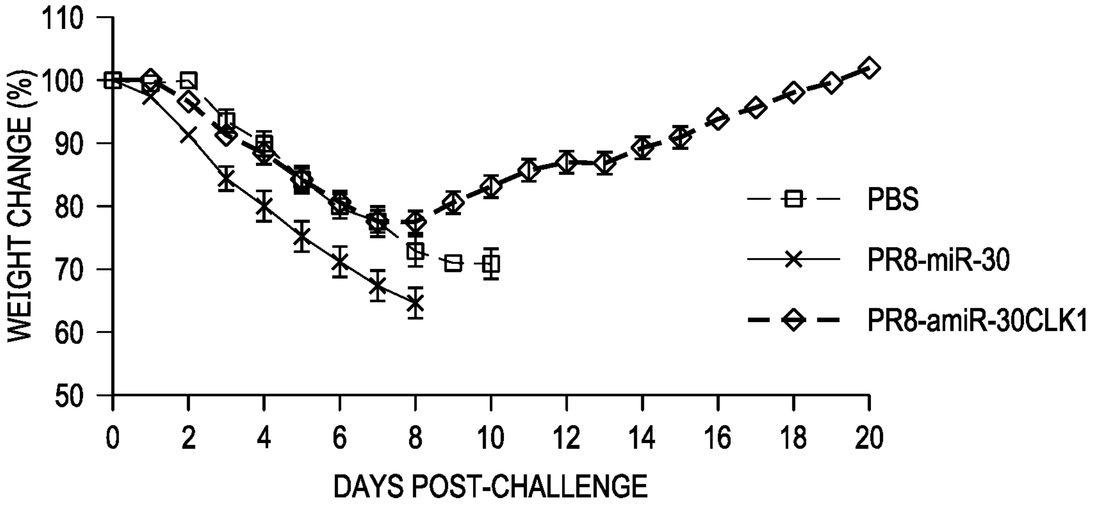
FIGS. 5A and 5B show the therapeutic effects of host CLK1-targetted SAIV, PR8-NA-amiR-30CLK1 in mice. 6-8 old Balb/c mice (n=10/group, 5 male and 5 female) were first intranasally infected with 20×MLD50 ($10^4$ PFU) wild-type PR8 virus. Six hours later, mice were intranasally dosed with $3\times10^5$ PFU of PR8-NA-amiR-30CLK viruses. Mouse weight changes (FIG. 5A) and survival rates (FIG. 5B) were recorded for 21 days.
Figure 5B:
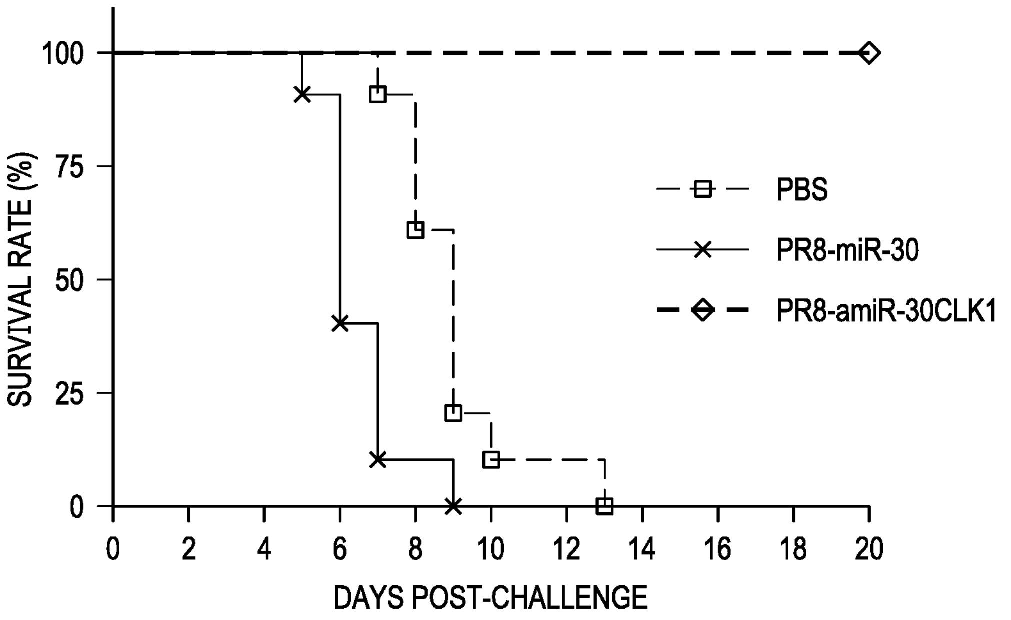

The inventors also evaluated the immunogenicity and protective efficacy of this host CLK1-targetted SAIV, PR8-NA-amiR-30CLK1, in mice. FIGS. 4A to 4D show that a single intranasal dose immunization with PR8-NA-amiR-30CLK1 elicited robust antibody response against influenza virus and protected mice against lethal challenge with wild type PR8 influenza viral challenge. Additionally, PR8-NA-amiR-30CLK1 can also been used as an effective post exposure treatment against influenza virus infection (FIGS. 5A and 5B).

Figure 6:
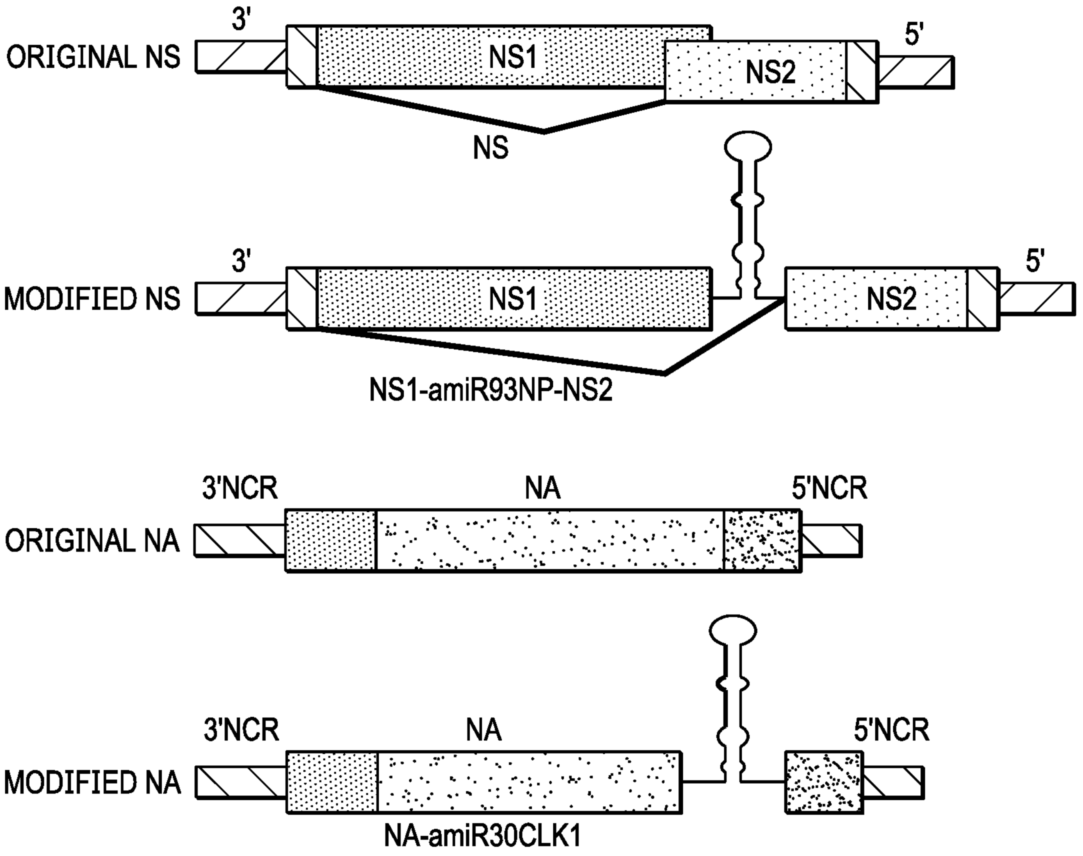
FIG. 6. Schematic representation of engineered gene segments of NA and NS in the dual targeted self-attenuated influenza virus. Engineered NA gene segment of influenza virus expresses functional artificial microRNA against NP gene of influenza virus. Engineered NS gene segment of influenza virus expresses functional artificial microRNA against host factor gene.
Figure 7:
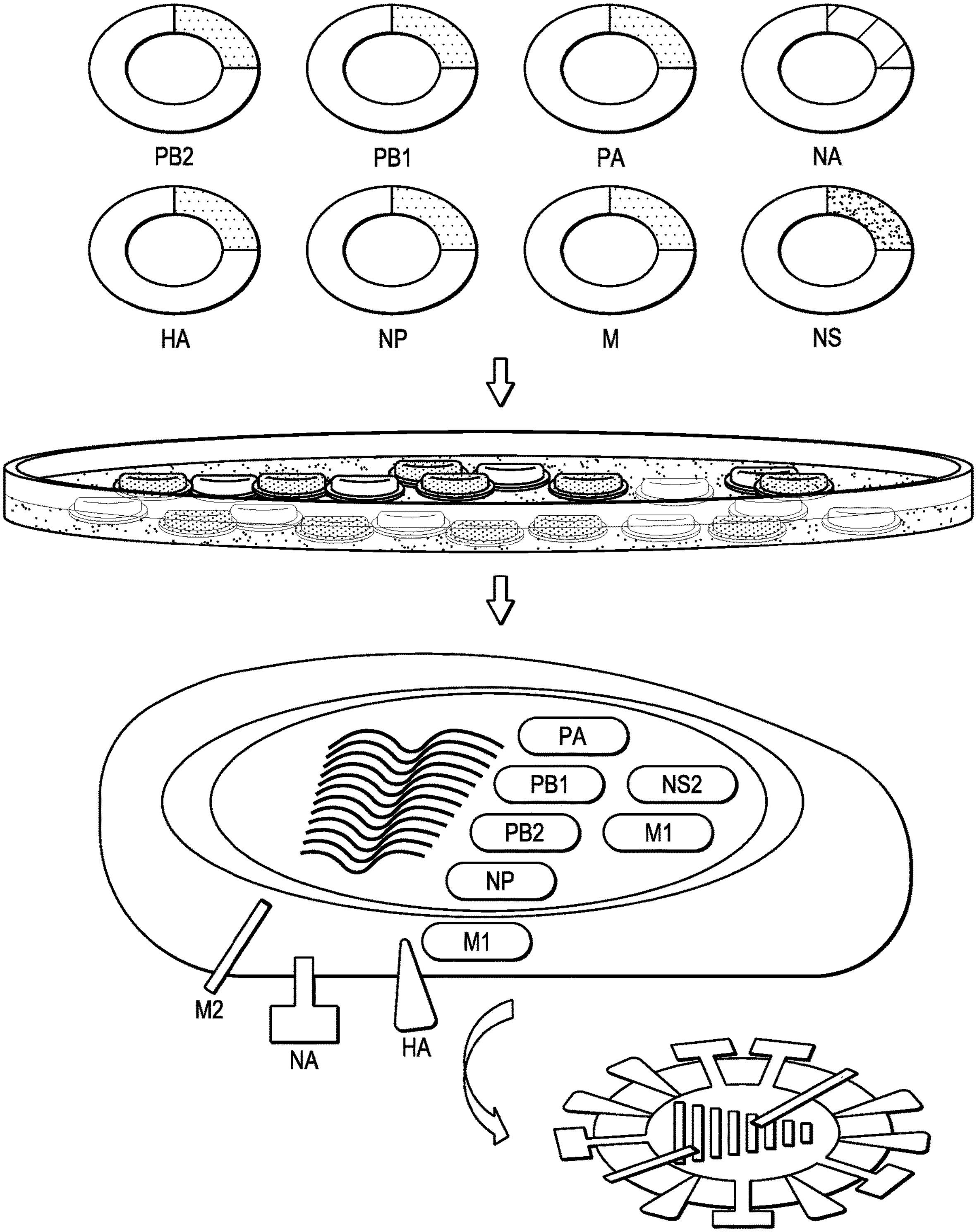
FIG. 7. Generation of the dual targeted SAIV by reverse genetics. The eight-plasmid system will be used for the generation of influenza A virus, PR8-NS-amiR93-NP/NA-amiR30-CLK1. The rescued influenza virus expresses functional artificial microRNAs against influenza virus NP gene and host CLK1 gene expression.
Figure 8:
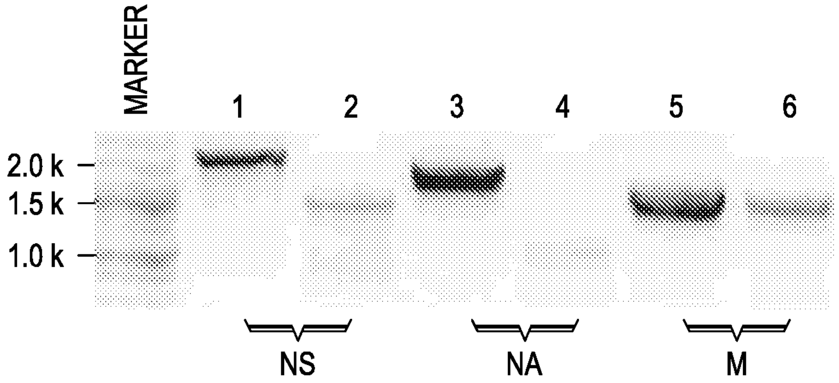
FIG. 8 Confirmation of rescued dual targeted SAIV, PR8-NS-amiR93-NP/NA-amiR30-CLK1 by RT-PCR. Viral RNA were isolated and used as template for RT-PCR to amplify specific NS, NA, and M fragments. Lanes 1, 3, 5 were the PCR products of PR8-NS-amiR93-NP/NA-amiR30-CLK1 influenza virus, while Lanes 2, 4, 6 were the PCR products of PR8 wild influenza virus. Lanes 1, 2 amplified NS fragment, Lanes 3, 4 amplified NA fragment, and Lanes 5, 6 amplified M fragment. Modified influenza virus generated larger NS, NA fragments compared to wild type PR8, and M fragment was not changed.

Thus, the present inventors have shown that the host CLK1-targetted SAIV, PR8-NA-amiR-30CLK1, is a prophylactic vaccine and anti-influenza therapeutic in mouse model of influenza infection. The present inventors have also designed and constructed a dual-targeted SAIV, PR8-NS-amiR93-NP/NA-amiR30-CLK1 expressing two amiRNA in two influenza viral segments (NS and NA), that can silence one viral NP gene and one host CLK1 gene (FIGS. 6, 7, and 8).

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps, namely, an isolated virus comprising a viral genome that expresses one or more viral antigens; and an artificial microRNA 30 (amiR-30) or other microRNA expression cassette inserted into a viral neuraminidase (NA) or a viral non-structural (NS) gene segment that expresses an amiR-30 or other microRNA that specifically inhibits the expression of a host gene essential for influenza virus replication in host cells. In one example, the present invention includes a method of making a live, self-attenuated virus comprising: obtaining isolated virus comprising a viral genome that expresses one or more viral antigens; and an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells.

In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention, namely, an isolated virus consisting essentially of a viral genome that expresses one or more viral antigens; and an artificial microRNA 30 (amiR-30) or other microRNA expression cassette inserted into a viral neuraminidase (NA) or a viral non-structural (NS) gene segment that expresses an amiR-30 or other microRNA that specifically inhibits the expression of a host gene essential for influenza virus replication in host cells, that do not materially affect the character or function of the claimed invention. In one example, the present invention includes a method of making a live, self-attenuated virus consisting essentially of: obtaining isolated virus comprising a viral genome that expresses one or more viral antigens; and an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells.

As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only, namely, an isolated virus consisting of a viral genome that expresses one or more viral antigens; and an artificial microRNA 30 (amiR-30) or other microRNA expression cassette inserted into a viral neuraminidase (NA) or a viral non-structural (NS) gene segment that expresses an amiR-30 or other microRNA that specifically inhibits the expression of a host gene essential for influenza virus replication in host cells. In one example, the present invention includes a method of making a live, self-attenuated virus consisting of: obtaining isolated virus comprising a viral genome that expresses one or more viral antigens; and an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, “about”, “substantial” or “substantially” refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as “about” may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words “means for” or “step for” are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Ison M G. Antivirals and resistance: influenza virus. Current opinion in virology. 2011; 1(6): 563-73. Epub 2012 Mar. 24. doi: 51879-6257(11)00106-4 [pii] 10.1016/j.coviro.2011.09.002 [doi]. PubMed PMID: 22440914.
2. Dugan V G, Blanton L, Elal A I A, Alabi N, Barnes J, Brammer L, et al. Update: Influenza Activity—United States, Oct. 1-Nov. 25, 2017. MMWR Morb Mortal Wkly Rep. 2017; 66(48):1318-26. Epub 2017 Dec. 8. doi: 10.15585/mmwr.mm6648a2. PubMed PMID: 29216030; PubMed Central PMCID: PMCPMC5757637.
3. Li J, Arevalo M T, Diaz-Arevalo D, Chen Y, Choi J G, Zeng M. Generation of a safe and effective live viral vaccine by virus self-attenuation using species-specific artificial microRNA. J Control Release. 2015; 207:70-6. Epub 2015 Apr. 11 06:00. PubMed PMID: 25858415.
4. Konig R, Stertz S, Zhou Y, Inoue A, Hoffmann H H, Bhattacharyya S, et al. Human host factors required for influenza virus replication. Nature. 2010; 463(7282):813-7. Epub 2009 Dec. 23. doi: nature08699 [pii] 10.1038/nature08699 [doi]. PubMed PMID: 20027183; PubMed Central PMCID: PMC2862546.
5. Karlas A, Machuy N, Shin Y, Pleissner K P, Artarini A, Heuer D, et al. Genome-wide RNAi screen identifies human host factors crucial for influenza virus replication. Nature. 2010; 463(7282):818-22. Epub 2010 Jan. 19. doi: nature08760 [pii]10.1038/nature08760 [doi]. PubMed PMID: 20081832.
6. Hensley S E. Challenges of selecting seasonal influenza vaccine strains for humans with diverse pre-exposure histories. Current opinion in virology. 2014; 8C:85-9. Epub 2014 Aug. 12. doi: S1879-6257(14)00152-7 [pii] 10.1016/j.coviro.2014.07.007 [doi]. PubMed PMID: 25108824.
7. Arèvalo M T, Navarro A, Arico C D, Li J, Alkhatib O, Chen S, et al. Targeted Silencing of Anthrax Toxin Receptors Protects against Anthrax Toxins. The Journal of biological chemistry. 2014; 289(22):15730-8. Epub 2014 Apr. 20. doi: M113.538587 [pii]10.1074/jbc.M113.538587 [doi]. PubMed PMID: 24742682.
8. Jagger B W, Wise H M, Kash J C, Walters K A, Wills N M, Xiao Y L, et al. An overlapping protein-coding region in influenza A virus segment 3 modulates the host response. Science (New York, N.Y.). 2012; 337(6091): 199-204. Epub 2012 Jun. 30. doi: 10.1126/science.1222213. PubMed PMID: 22745253.
9. Zeng M, Li J, inventors; Texas Tech University System, assignee. New live attenuated viral vaccine created by self-attenuation with species-specific artificial microRNA. PCT/US2015/055495. USA 2014.
10. Schmid S, Zony L C, tenOever BR. A versatile RNA vector for delivery of coding and noncoding RNAs. J Virol. 2014; 88(4):2333-6. doi: 10.1128/N1.03267-13. PubMed PMID: 24307584; PubMed Central PMCID: PMC3911536.
11. Perez J T, Pham A M, Lorini M H, Chua M A, Steel J, tenOever BR. MicroRNA-mediated species-specific attenuation of influenza A virus. Nat Biotechnol. 2009; 27(6):572-6. Epub 2009 Jun. 2. doi: 10.1038/nbt.1542. PubMed PMID: 19483680.
12. Li J, Arevalo M T, Chen Y, Chen S, Zeng M. T-cell-mediated cross-strain protective immunity elicited by prime-boost vaccination with a live attenuated influenza vaccine. International journal of infectious diseases: IJID: official publication of the International Society for Infectious Diseases. 2014; 27C:37-43. doi: 10.1016/j.ijid.2014.05.016. PubMed PMID: 25172265.
13. Bouvier N M, Lowen A C. Animal Models for Influenza Virus Pathogenesis and Transmission. Viruses. 2010; 2(8):1530-63. Epub 2010 Jan. 1. doi: 10.3390/v20801530 [doi]. PubMed PMID: 21442033; PubMed Central PMCID: PMC3063653.
14. Thangavel R R, Bouvier N M. Animal models for influenza virus pathogenesis, transmission, and immunology. Journal of immunological methods. 2014. doi: 10.1016/j.jim.2014.03.023. PubMed PMID: 24709389.
15. Kitano M, Itoh Y, Kodama M, Ishigaki H, Nakayama M, Ishida H, et al. Efficacy of single intravenous injection of peramivir against influenza B virus infection in ferrets and cynomolgus macaques. Antimicrobial agents and chemotherapy. 2011; 55(11):4961-70. Epub 2011 Aug. 17. doi: AAC.00412-11 [pii]10.1128/AAC.00412-11 [doi]. PubMed PMID: 21844317; PubMed Central PMCID: PMC3195024.
16. Li J, Arevalo M T, Chen Y, Posadas O, Smith J A, Zeng M. Intranasal immunization with influenza antigens conjugated with cholera toxin subunit B stimulates broad spectrum immunity against influenza viruses. Human vaccines & immunotherapeutics. 2014; 10(5):1211-20. doi: 10.4161/hv.28407. PubMed PMID: 24632749.
17. Reed L J, Muench H. A simple method for estimating fifty percent endpoints. Am J Hyg. 1938; 27:493-7.
18. Rimmelzwaan G F, McElhaney J E. Correlates of protection: novel generations of influenza vaccines. Vaccine. 2008; 26 Suppl 4:D41-4. PubMed PMID: 19230158.
19. Li C K, Rappuoli R, Xu X N. Correlates of protection against influenza infection in humans—on the path to a universal vaccine? Current opinion in immunology. 2013; 25(4):470-6. doi: 10.1016/j.coi.2013.07.005. PubMed PMID: 23948572.
20. Corti D, Lanzavecchia A. Broadly neutralizing antiviral antibodies. Annu Rev Immunol. 2013; 31:705-42. doi: 10.1146/annurev-immunol-032712-095916. PubMed PMID: 23330954.
21. Rimmelzwaan G F, Fouchier R A, Osterhaus A D. Influenza virus-specific cytotoxic T lymphocytes: a correlate of protection and a basis for vaccine development. Curr Opin Biotechnol. 2007; 18(6):529-36. doi: 10.1016/j.copbio.2007.11.002. PubMed PMID: 18083548.
22. Sridhar S, Begom S, Bermingham A, Hoschler K, Adamson W, Carman W, et al. Cellular immune correlates of protection against symptomatic pandemic influenza. Nat Med. 2013; 19(10):1305-12. doi: 10.1038/nm.3350. PubMed PMID: 24056771.
23. Rowe T, Abernathy R A, Hu-Primmer J, Thompson W W, Lu X, Lim W, et al. Detection of antibody to avian influenza A (H5N1) virus in human serum by using a combination of serologic assays. J Clin Microbiol. 1999; 37(4):937-43.
24. Harmon M W, Rota P A, Walls H H, Kendal A P. Antibody response in humans to influenza virus type B host-cell-derived variants after vaccination with standard (egg-derived) vaccine or natural infection. J Clin Microbiol. 1988; 26(2):333-7.
25. Keitel W A, Dekker C L, Mink C, Campbell J D, Edwards K M, Patel S M, et al. Safety and immunogenicity of inactivated, Vero cell culture-derived whole virus influenza A/H5N1 vaccine given alone or with aluminum hydroxide adjuvant in healthy adults. Vaccine. 2009; 27(47): 6642-8. Epub 2009 Sep. 24. doi: 50264-410X(09)00401-0 [pii]10.1016/j.vaccine.2009.03.015 [doi]. PubMed PMID: 19773098; PubMed Central PMCID: PMC3022490.
26. Sasaki S, He X S, Holmes T H, Dekker C L, Kemble G W, Arvin A M, et al. Influence of prior influenza vaccination on antibody and B-cell responses. PLoS One. 2008; 3(8):e2975. Epub 2008 Aug. 21. doi: 10.1371/journal.pone.0002975 [doi]. PubMed PMID: 18714352; PubMed Central PMCID: PMC2500171.
27. Noah D L, Hill H, Hines D, White E L, Wolff M C. Qualification of the hemagglutination inhibition assay in support of pandemic influenza vaccine licensure. Clin Vaccine Immunol. 2009; 16(4):558-66. Epub 2009 Feb. 20. doi: CVI.00368-08 [pii] 10.1128/CVI.00368-08 [doi]. PubMed PMID: 19225073; PubMed Central PMCID: PMC2668270.
28. Jackson L A, Patel S M, Swamy G K, Frey S E, Creech C B, Munoz F M, et al. Immunogenicity of an inactivated monovalent 2009 H1N1 influenza vaccine in pregnant women. J Infect Dis. 2011; 204(6):854-63. Epub 2011 Aug. 19. doi: jir440 [pii]10.1093/infdis/jir440 [doi]. PubMed PMID: 21849282; PubMed Central PMCID: PMC3156926.
29. Cellerai C, Perreau M, Rozot V, Enders F B, Pantaleo G, Harari A. Proliferation capacity and cytotoxic activity are mediated by functionally and phenotypically distinct virus-specific CD8 T cells defined by interleukin-7R{alpha} (CD127) and perforin expression. J Virol. 2010; 84(8):3868-78. Epub 2010 Feb. 5. doi: 10.1128/JVI.02565-09. PubMed PMID: 20130059; PubMed Central PMCID: PMC2849500.
30. Harari A, Enders F B, Cellerai C, Bart P A, Pantaleo G. Distinct profiles of cytotoxic granules in memory CD8 T cells correlate with function, differentiation stage, and antigen exposure. J Virol. 2009; 83(7):2862-71. Epub 2009 Jan. 30. doi: 10.1128/JVI.02528-08. PubMed PMID: 19176626; PubMed Central PMCID: PMC2655574.
31. Boltz D A, Rehg J E, McClaren J, Webster R G, Govorkova E A. Oseltamivir prophylactic regimens prevent H5N1 influenza morbidity and mortality in a ferret model. J Infect Dis. 2008; 197(9):1315-23. doi: 10.1086/586711. PubMed PMID: 18422444.
32. Duan S, Boltz D A, Seiler P, Li J, Bragstad K, Nielsen L P, et al. Oseltamivir-resistant pandemic H1N1/2009 influenza virus possesses lower transmissibility and fitness in ferrets. PLoS pathogens. 2010; 6(7):e1001022. doi: 10.1371/journal.ppat.1001022. PubMed PMID: 20686654; PubMed Central PMCID: PMC2912389.
33. Yen H L, Aldridge J R, Boon A C, Ilyushina N A, Salomon R, Hulse-Post D J, et al. Changes in H5N1 influenza virus hemagglutinin receptor binding domain affect systemic spread. Proc Natl Acad Sci USA. 2009; 106(1):286-91. doi: 10.1073/pnas.0811052106. PubMed PMID: 19116267; PubMed Central PMCID: PMC2629220.
34. Music N, Reber A J, Lipatov A S, Kamal R P, Blanchfield K, Wilson J R, et al. Influenza vaccination accelerates recovery of ferrets from lymphopenia. PLoS One. 2014; 9(6):e100926. doi: 10.1371/journal.pone.0100926. PubMed PMID: 24968319; PubMed Central PMCID: PMC4072694.
35. D'Cruz O J, Uckun F M. Intravaginal toxicity studies of a gel-microemulsion formulation of spermicidal vanadocenes in rabbits. Toxicol Appl Pharmacol. 2001; 170(2): 104-12.
36. D'Cruz O J, Waurzyniak B, Uckun F M. Mucosal toxicity studies of a gel formulation of native pokeweed antiviral protein. Toxicol Pathol. 2004; 32(2):212-21.
37. Yuhas Y, Shulman L, Weizman A, Kaminsky E, Vanichkin A, Ashkenazi S. Involvement of tumor necrosis factor alpha and interleukin-1beta in enhancement of pentylenetetrazole-induced seizures caused by *Shigella dysenteriae*. Infect Immun. 1999; 67(3): 1455-60.
38. Donnelly S, Loscher C E, Lynch M A, Mills K H. Whole-cell but not acellular pertussis vaccines induce convulsive activity in mice: evidence of a role for toxin-induced interleukin-1beta in a new murine model for analysis of neuronal side effects of vaccination. Infect Immun. 2001; 69(7):4217-23.
39. Abraham S, Pahwa R, Ye C, Choi J G, Pahwa S, Jaggaiahgari S, et al. Long-term engraftment of human natural T regulatory cells in NOD/SCID IL2rgammac (null) mice by expression of human IL-2. PLoS One. 2012; 7(12):e51832. Epub 2012 Dec. 29. doi: 10.1371/journal.pone.0051832 PONE-D-12-07866 [pii]. PubMed PMID: 23272176; PubMed Central PMCID: PMC3525660.
40. Layton R C, Gigliotti A, Armijo P, Myers L, Knight J, Donart N, et al. Enhanced immunogenicity, mortality protection, and reduced viral brain invasion by alum adjuvant with an H5N1 split-virion vaccine in the ferret. PLoS One. 2011; 6(6):e20641. Epub 2011 Jun. 21. doi: 10.1371/journal.pone.0020641. PubMed PMID: 21687736; PubMed Central PMCID: PMC3110201.

41. Layton R C, Petrovsky N, Gigliotti A P, Pollock Z, Knight J, Donart N, et al. Delta inulin polysaccharide adjuvant enhances the ability of split-virion H5N1 vaccine to protect against lethal challenge in ferrets. Vaccine. 2011; 29(37):6242-51. Epub 2011 Oct. 9. doi: 10.1016/j.vaccine.2011.06.078. PubMed PMID: 21736913; PubMed Central PMCID: PMCPMC3156374.

42. AVMA. AVMA Guidelines for the Euthanasia of Animals: 2013 Edition. Schaumburg, Ill. 2013.

What is claimed is:

1. A live, self-attenuated virus comprising:

a viral genome that expresses one or more viral antigens; and an artificial microRNA 30 (amiR-30 expression cassette) inserted into a viral neuraminidase (NA) or a viral non-structural (NS) gene segment of the viral genome, as applicable, of the live self-attenuated virus to express an amiR-30 that specifically inhibits the expression of a host gene essential for virus replication in host cells.

2. The virus of claim 1, wherein the isolated virus further comprises a mammalian-specific artificial microRNA 93 (amiR-93) expression cassette inserted into the viral neuraminidase (NA) or the viral non-structural (NS) gene segment that inhibits viral nucleoprotein (NP) gene expression.

3. The virus of claim 1, wherein the amiR-30 comprises a sequence that targets expression of the host gene in a miR-30 backbone.

4. The virus of claim 1, wherein the host gene is at least one of CDC-Like Kinase 1 (CLK1), SON DNA binding protein (SON), cyclin-dependent kinase inhibitor 1B (Cdkn1b), calcium/calmodulin-dependent protein kinase (CaM kinase) II beta (CAMK2B), or vacuolar ATPase (vATPase).

5. The virus of claim 1, wherein the microRNA is not expressed in avian cells; or the microRNA comprises a miR-93 backbone-based cassette for species-specific microRNA expression.

6. The virus of claim 1, wherein the influenza virus at least one of: expresses one or more viral antigens that confer protection against H1N1, pandemic H1N1, and H3N2; the virus is packaged into a vaccine; the virus is adapted for pulmonary, oral, nasal, transcutaneous, or mucosal administration; or the virus is adapted for use as a vaccine for prevention of infectious diseases or as therapeutic for post infection treatment.

7. The virus of claim 1, wherein the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens, or confers protective immunity to the virus.

8. The virus of claim 2, wherein the mature miR-93 loop is replaced with sequence within the mature miR-93 loop was replaced with one of the following sequences:

(SEQ ID NO: 2)
amiR-93-NP
GTTAACTCCCGTCTTGGACCTCAGTCCTGGGGGCTCACTCCTCTGCA

TTGTCTCCGAAGTGTGATTACCCAACCTTGGAGCAATGGCAGAGGAA

AAGAGCCCCCGGGACACGTTCTCTCTGCCAATTCTCGAG (SEQ ID NO: 3)
amiR-93-SON
TCCCGTCTTGGACCTCAGTCCTGGGGGCTCGTGAAATAGTACAAGGT

GCACAGTGTGATTACCCAACCTGGCACTTGTAGCTATTTCTGTGAGC

CCCCGGGACACGTTCTCTCTGCCAATT

-continued (SEQ ID NO: 5)
amiR-30-CLK1
GAAGGTATATTGCTGTTGACAGTGAGCGACTCCCAATGAGGTCAAAG

AGAAGCTGTGAAGCCACAGATGGGCTTCTCTTTCCTCATTGGGAGCT

GCCTACTGCCTCGGACTTCAAGGGGCTAC (SEQ ID NO: 6)
amiR-30-Cdkn1b
GAAGGTATATTGCTGTTGACAGTGAGCGACTAGAAGAATCGTCGGTT

GCAGGCTGTGAAGCCACAGATGGGCCTGCAACCCGATTCTTCTAGCT

GCCTACTGCCTCGGACTTCAAGGGGCTAC (SEQ ID NO: 7)
amiR-30-CAMK2B
GAAGGTATATTGCTGTTGACAGTGAGCGACCACATCTGGTCTTGTTT

TTCTGCTGTGAAGCCACAGATGGGCAGAAAAACGACCAGATGTGGCT

GCCTACTGCCTCGGACTTCAAGGGGCTAC (SEQ ID NO: 8)
amiR-30-vATPase (ATP6V0C)
GAAGGTATATTGCTGTTGACAGTGAGCGACTAAGGTTATAGATAGCT

GGGAGCTGTGAAGCCACAGATGGGCTCCCAGCTCTATAACCTTAGCT

GCCTACTGCCTCGGACTTCAAGGGGCTAC.

9. The virus of claim 1, wherein the virus has an $EID_{50}$ of 10 or less.

10. The virus of claim 1, wherein the virus comprises multiple artificial miRNA expression cassettes.

11. The virus of claim 1, wherein the virus is selected from an influenza, human immunodeficiency virus (HIV), hepatitis B virus (HBV), West Nile virus, Dengue Fever, or Zika virus.

12. A method of making a live, self-attenuated virus comprising:

obtaining an isolated virus comprising a viral genome that expresses one or more viral antigens; and inserting into the viral genome an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells.

13. The method of claim 12, wherein the isolated virus further comprises a mammalian-specific artificial microRNA 93 (amiR-93) expression cassette inserted into the viral neuraminidase (NA) or the viral non-structural (NS) gene segment that inhibits viral nucleoprotein (NP) gene expression.

14. The method of claim 12, wherein the amiR-30 comprises a sequence that targets expression of the host gene in a miR-30 backbone.

15. The method of claim 12, wherein the host gene is at least one of CDC-Like Kinase 1 (CLK1), SON DNA binding protein (SON), cyclin-dependent kinase inhibitor 1B (Cdkn1b), calcium/calmodulin-dependent protein kinase (CaM kinase) IIbeta (CAMK2B), or vacuolar ATPase (vATPase).

16. The method of claim 12, wherein the microRNA is not expressed in avian cells or the microRNA comprises a miR-93 backbone-based cassette for species-specific microRNA expression.

17. The method of claim 12, wherein the virus at least one of: expresses one or more additional viral antigens that confer protection against H1N1, pandemic H1N1, and H3N2; the virus is packaged into a vaccine; the virus is adapted for pulmonary, oral, nasal, transcutaneous, or mucosal administration; or the virus is adapted to prevent an infectious diseases or as therapeutic for post infection treatment.

18. The method of claim 12, wherein the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens, or confers protective immunity to the virus.

19. The method of claim 13, wherein the mature miR-93 loop is replaced with sequence within the mature miR-93 loop was replaced with one of the following sequences:

(SEQ ID NO: 2)
amiR-93-NP
GTTAACTCCCGTCTTGGACCTCAGTCCTGGGGGCTCACTCCTCTGCA

TTGTCTCCGAAGTGTGATTACCCAACCTTGGAGCAATGGCAGAGGAA

AAGAGCCCCCGGGACACGTTCTCTCTGCCAATTCTCGAG (SEQ ID NO: 3)
amiR-93-SON
TCCCGTCTTGGACCTCAGTCCTGGGGGCTCGTGAAATAGTACAAGGT

GCACAGTGTGATTACCCAACCTGGCACTTGTAGCTATTTCTGTGAGC

CCCCGGGACACGTTCTCTCTGCCAATT (SEQ ID NO: 5)
amiR-30-CLK1
GAAGGTATATTGCTGTTGACAGTGAGCGACTCCCAATGAGGTCAAAG

AGAAGCTGTGAAGCCACAGATGGGCTTCTCTTTCCTCATTGGGAGCT

GCCTACTGCCTCGGACTTCAAGGGGCTAC (SEQ ID NO: 6)
amiR-30-Cdkn1b
GAAGGTATATTGCTGTTGACAGTGAGCGACTAGAAGAATCGTCGGTT

GCAGGCTGTGAAGCCACAGATGGGCCTGCAACCCGATTCTTCTAGCT

GCCTACTGCCTCGGACTTCAAGGGGCTAC

-continued (SEQ ID NO: 7)
amiR-30-CAMK2B
GAAGGTATATTGCTGTTGACAGTGAGCGACCACATCTGGTCTTGTTT

TTCTGCTGTGAAGCCACAGATGGGCAGAAAAACGACCAGATGTGGCT

GCCTACTGCCTCGGACTTCAAGGGGCTAC (SEQ ID NO: 8)
amiR-30-vATPase (ATP6V0C)
GAAGGTATATTGCTGTTGACAGTGAGCGACTAAGGTTATAGATAGCT

GGGAGCTGTGAAGCCACAGATGGGCTCCCAGCTCTATAACCTTAGCT

GCCTACTGCCTCGGACTTCAAGGGGCTAC.

20. The method of claim 12, wherein the virus has an $EID_{50}$ of 10 or less.

21. The method of claim 12, wherein the virus comprises multiple artificial miRNA expression cassettes.

22. The method of claim 12, wherein the virus is selected from an influenza, human immunodeficiency virus (HIV), hepatitis B virus (HBV), West Nile virus, Dengue Fever, or Zika virus.

23. The method of claim 12, further comprising testing the live, self-attenuated virus by:

determining if the virus propagates in the viral propagation cell but is attenuated in the viral target species cell.

24. The virus of claim 1, further comprising:

one or more adjuvants, excipients, or buffers, wherein the therapeutic vaccine is adapted for at least one of: pulmonary, intraalveolar, nasal, transcutaneous, or mucosal administration.

25. A method of treating a patient with a therapeutic vaccine comprising:

identifying that the patient is in need of prophylaxis or treatment of an active viral infection; and providing the patient with a vaccine comprising a live, attenuated virus that comprises an artificial microRNA 30 (amiR-30) expression cassette inserted into a viral neuraminidase (NA) or a viral non-structural (NS) gene segment that expresses an amiR-30 that specifically inhibits the expression of a host gene essential for influenza virus replication in host cells, in an amount effective to provide prophylaxis against, or treatment of, an active viral infection.

* * * * *